US010219883B2

(12) United States Patent
van der Steen et al.

(10) Patent No.: US 10,219,883 B2
(45) Date of Patent: *Mar. 5, 2019

(54) METHODS FOR USE OF SEX SORTED SEMEN TO IMPROVE GENETIC MANAGEMENT IN SWINE

(71) Applicant: Inguran, LLC, Navasota, TX (US)

(72) Inventors: Hein van der Steen, Evesham (GB); Gregg Bevier, Navasota, TX (US)

(73) Assignee: Inguran, LLC, Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/853,010

(22) Filed: Dec. 22, 2017

(65) Prior Publication Data

US 2018/0161137 A1    Jun. 14, 2018

Related U.S. Application Data

(63) Continuation of application No. 14/090,979, filed on Nov. 26, 2013, now Pat. No. 9,888,990, which is a continuation-in-part of application No. 13/840,598, filed on Mar. 15, 2013, now Pat. No. 9,433,195.

(60) Provisional application No. 61/656,446, filed on Jun. 6, 2012.

(51) Int. Cl.
| | |
|---|---|
| A61K 48/00 | (2006.01) |
| A61D 19/02 | (2006.01) |
| A61B 1/04 | (2006.01) |
| A61B 1/313 | (2006.01) |
| A61B 6/12 | (2006.01) |
| A61B 6/00 | (2006.01) |
| A61K 35/52 | (2015.01) |

(52) U.S. Cl.
CPC ............. *A61D 19/027* (2013.01); *A61B 1/04* (2013.01); *A61B 1/3132* (2013.01); *A61B 6/12* (2013.01); *A61B 6/485* (2013.01); *A61K 35/52* (2013.01)

(58) Field of Classification Search
CPC .................................. A61D 19/27; A61B 1/04
See application file for complete search history.

(56) References Cited

U.S. PATENT DOCUMENTS

| | | | |
|---|---|---|---|
| 5,651,330 A | 7/1997 | Jewett | |
| 6,071,689 A | 6/2000 | Seidel | |
| 6,149,867 A | 11/2000 | Seidel | |
| 6,263,745 B1 | 7/2001 | Buchanan | |
| 6,357,307 B2 | 3/2002 | Buchanan | |
| 6,372,422 B1 | 4/2002 | Seidel | |
| 6,524,860 B1 | 2/2003 | Seidel | |
| 6,604,435 B2 | 8/2003 | Buchanan | |
| 6,617,107 B1 | 9/2003 | Dean | |
| 6,695,767 B2 | 2/2004 | Garcia et al. | |
| 6,746,873 B1 | 6/2004 | Buchanan | |
| 6,782,768 B2 | 8/2004 | Buchanan | |
| 6,819,411 B1 | 11/2004 | Sharpe | |
| 7,094,527 B2 | 8/2006 | Seidel | |
| 7,169,548 B2 | 1/2007 | Maxwell | |
| 7,195,920 B2 | 3/2007 | Seidel | |
| 7,208,265 B1 | 4/2007 | Schenk | |
| 7,221,453 B2 | 5/2007 | Sharpe | |
| 7,325,690 B2 | 2/2008 | Cognard | |
| 7,335,507 B2 | 2/2008 | Anzar | |
| 7,371,517 B2 | 5/2008 | Evans | |
| 7,586,604 B2 | 9/2009 | Sharpe | |
| 7,618,770 B2 | 11/2009 | Schenk | |
| 7,713,687 B2 | 5/2010 | Seidel | |
| 7,723,116 B2 | 5/2010 | Evans | |
| 7,758,811 B2 | 7/2010 | Durack | |
| 7,771,921 B2 | 8/2010 | Seidel | |
| 7,799,569 B2 | 9/2010 | Durack | |
| 7,820,425 B2 | 10/2010 | Schenk | |
| 7,833,147 B2 | 11/2010 | Graham | |

(Continued)

FOREIGN PATENT DOCUMENTS

| | | |
|---|---|---|
| EP | 1017987 B1 | 6/2005 |
| EP | 1554180 B1 | 1/2007 |

(Continued)

OTHER PUBLICATIONS

Martinez, E.A., et al., "Successful non-surgical deep intrauterine insemination with small numbers of spermatozoa in sows", Reproduction—online Aug. 2001, 122 289-296.

Martinez, E.A., et al., "An update on reproductive technologies with potential short-term application in pig production", Reprod Domest Anim. Aug. 2005; 40(4): 300-9.

Martinez, E.A., et al., "Minimum number of spermatozoa required for normal fertility after deep intrauterine insemination in non-sedated sows", Reproduction, Jan. 1, 2002, 123 163-170.

Martinez, E.A., et al. "Incidence of Unilateral Fertilizations after Low Dose Deep Intrauterine Insemination in Spontaneously Ovulating Sows under Field Conditions", Reproduction in Domestic Animals, vol. 41, Issue1, pp. 41-47, Feb. 2006.

(Continued)

*Primary Examiner* — Marcia S Noble
(74) *Attorney, Agent, or Firm* — Ryan Christensen; Hashim Rahman

(57) ABSTRACT

The invention relates to methods of increasing genetic merit of swine by establishing a plurality of mating subtypes for a line of swine, and determining a percentage of progeny that are male for each of the mating subtypes, or a percentage of progeny that are female for each of the mating subtypes, that would result, relative to a control, in an increase in genetic merit in the line; the invention further relates to sorting a sperm cell sample from a male swine in one of the mating subtypes into one or more subpopulations of sperm cells, wherein a majority of sperm cells in a subpopulation of sperm cells bear X chromosomes or Y chromosomes, and inseminating one or more female swine in the one of the mating subtypes with the subpopulation of sperm cells to achieve the percentage of progeny that are male, or the percentage of progeny that are female, determined to increase genetic merit relative to the control.

4 Claims, 3 Drawing Sheets

(56) References Cited

U.S. PATENT DOCUMENTS

| | | | |
|---|---|---|---|
| 7,838,210 | B2 | 11/2010 | Ludwig |
| 7,855,078 | B2 | 12/2010 | Evans |
| 7,892,725 | B2 | 2/2011 | Graham |
| 7,893,315 | B2 | 2/2011 | Chung et al. |
| 7,929,137 | B2 | 4/2011 | Sharpe |
| 7,943,384 | B2 | 5/2011 | Durack |
| 7,981,682 | B2 | 7/2011 | Evans |
| 7,998,700 | B2 | 8/2011 | Ludwig |
| 8,060,353 | B2 | 11/2011 | Salinas |
| 8,080,422 | B2 | 12/2011 | Neas |
| 8,338,098 | B2 | 12/2012 | Khatib et al. |
| 2003/0087860 | A1* | 5/2003 | Mileham ............... C12N 9/1205 514/44 A |
| 2005/0245902 | A1 | 11/2005 | Cornish et al. |
| 2008/0028478 | A1 | 1/2008 | Buttram et al. |
| 2012/0295247 | A1 | 11/2012 | Liegeois |
| 2012/0301868 | A1 | 11/2012 | Pascual |
| 2013/0331693 | A1 | 12/2013 | Moreno et al. |

FOREIGN PATENT DOCUMENTS

| | | |
|---|---|---|
| EP | 1608382 B1 | 8/2007 |
| EP | 1044262 B1 | 10/2008 |
| EP | 1608963 B1 | 12/2009 |
| EP | 1730523 B1 | 1/2010 |
| EP | 1238261 B1 | 5/2010 |
| EP | 1546325 B1 | 8/2011 |
| WO | 03096799 A2 | 11/2003 |
| WO | 2004088283 A2 | 10/2004 |
| WO | 2010034871 A1 | 1/2010 |
| WO | 2010025404 A1 | 3/2010 |
| WO | 2010124220 A1 | 10/2010 |
| WO | 2012002823 A2 | 5/2012 |

OTHER PUBLICATIONS

Medeiros, CM, et al., Current status of sperm cryopreservation: why isn't it better? Theriogenology, Jan. 1, 2002; 57(1): 327-44.

Rath, D., et al. "Birth of female piglets following intrauterine insemination of a sow using flow cytometrically sexed boar semen", Veterinary Record 2003: 152: 13 400-401.

Roca, Jordi, et al. "Fertility of weaned sows after deep intrauterine insemination with a reduced number of frozen-thawed spermatozoa", Theriogenology, vol. 60, Issue 1, Jun. 2003, pp. 77-87.

Tummaruk, P., et al., "Distribution of Spermatozoa and Embryos in the Female Reproductive Tract after Unilateral Deep Intra Uterine Insemination in the Pig", Reproduction in Domestic Animals, vol. 42, Issue 6, pp. 603-609, Dec. 2007.

Vazquez, Juan, M. et al., "Birth of piglets after deep intrauterine insemination with low cytometrically sorted boar spermatozoa", Theriogenology, vol. 59, Issue 7, Apr. 2003, pp. 1605-1614.

Vazquez, J.M., et al. "New developments in low-dose insemination technology", Theriogenology, vol. 70(8): Nov. 2008, pp. 1216-1224.

Wongtawan, Tuempong, et al., "Fertility after deep intra-uterine artificial insemination of concentrated low-volume boar semen doses", Theriogenology, vol. 65, Issue 4, Mar. 2006, pp. 773-787.

WIPO International Search Report and Written Opinion dated Jan. 14, 2014, issued in related PCT Application No. PCT/US13/44521 (45 pp).

Garcia, E.M., et al. "Improving the fertilizing ability of sex sorted boar spermatozoa", Theriogenoloy 68, (2007) 771-778.

Garner, Duane, "Flow cytometric sexing of mammalian sperm", Theriogenology 65 (2006) 943-957.

Dimitrov, S., et al. "Deep Intrauterine and Transcervical Insemination of Sows and Gilts", Trakia Journal of Sciences, vol. 5, No. 1, 2007, pp. 40-46.

Caballero, I., et al., "PSP-I/PSP-II spermadhesin exert a decapacitation effect on highly extended boar spermatozoa", Int. Jour. of Andrology 32, 505-513 (2008).

Ekhlasi-Hundrieser, M., et al., "point mutations abolishing the mannose-binding capability of boar spermadhesin AQN-1", Biochimica et Biophysica Acta 1784 (2008) 856-862.

Garcia, E.M., et al., "Localization and expression of spermadhesin PSP-1/PSP-II subunits in the reproductive organs of the boar" Int. Journal of Andrology 31, 408-417 (2007).

Romero, A., et al., "X-Ray Crystallographic Analysis of Boar PSP-I/PSP-II Complex A Zona Pellucida-Binding Protein", The Fate of the Male Germ Cell, Plenum Press, New York 1997, pp. 311-312.

Silva, L.D.M., et al. Laparoscopic Intrauterine Insemination in the Bitch, Theriogenology, 995, vol. 43, pp. 615-623.

PCT International Search Report and Written Opinion dated Feb. 11, 2014, issued in corresponding PCT Application No. PCT/US2013/072272 (13 pp).

Johnson, L.A., Sex Preselection in Swine: Altered Sex Ratios in Offspring Following Surgical Insemination of Flow Sorted X- and Y-Bearing Sperm, Reproduction in Domestic Animals, 1991, vol. 26; pp. 309-314.

Roberts, E., et al., A Study of Hybrid Vigor in a Cross Between Poland China and Duroc Jersey Swine. Journal of Agricultural Research, 1939, vol. 59; pp. 847-854.

Long, T.E, et al., "Estimating Genetic Merit. National Swine Improvement Federation (NSIF)" Swine Genetics Fact Sheet No. 8, 2003, pp. 1-4.

Vazquez, J.M., et al. "Low-Dose Insemination in Pigs: Problems and Possibilities", Reproduction in Domestic Animals, 2008, vol. 43, pp. 347-354.

Martinez, E.A., et al., "Successful Non-Surgical Deep Intrauterine Insemination With Small Numbers of Spermatozoa in Sows", Reproduction, 2001, vol. 122, pp. 289-296.

Schalla, S, et al., "Magnetic Resonance-Guided Cardiac Catheterization in a Swine Model of Atrial Septal Defect", Circulation 2003, vol. 108, pp. 1865-1870.

Blair, R.M., et al., Peri-oestrous hormone profiles, embryonic survival and variation in embryonic developments in gilts and primiparous sows, Journal of Reproduction and Fertility , 101, 167-173 (1994).

Dally, M.R., et al., Laparoscopic Artificial Insemination A Means to Improve Genetics Wool Production School, pp. 64-67(1992).

"Embryo and cloning technologies for custom genetic livestock production", MINITUBE, 1pp.

"Frozen-Thawed Semen", 1pp.

Garner, D.L., et al., "Viability Assessmnet of Mammalian Sperm Using SYBR-14 and Propidium Iodide", Biology of Reproduction , vol. 53, 276-284 (1995).

Gil, M.A., et al., "Pentoxifylline added to freezin or post-thaw extenders does not improve the survival or in vitro fertilising capacity of boar spermatozoa", Society for Reproduction and Fertility, Reproduction Mar. 1, 2010 139 557-564.

Gosalvez.L.F., et al., "Assessment of suitable porcine semen for freezing, according to the ejaculate characteristics in the Iberico x Landrace breed", Reproduction in Domestic Animals, 2002: 37(5): 282-4, Abstract 1pp.

IMV Technologies Catalog "Biotechnologies for pig reproduction", www.imv-technologies.com, 28pp.

Johnson, L.A., et al., "Use of Boar Spermatozoa for Artificial Insemination III. fecundity of Boar Spermatozoa Stored in Beltsville Liquid and Kiev Extenders for Three Days at 18C", Journal of Animal Science, 1982, 54: 132-136.

Kamp, G., et al. "Energy metabloism and intracellular pH in boar spermatozoa", Society for Reproduction and Fertility, 126, pp. 517-525 (2003).

Klinc, P., et al., "Reduction of Oxidative Stress in Bovine Spermatozoa During Flow Cytometric Sorting", Reproduction in Domestic Animals, vol. 42, pp. 63-67 (2007).

Knox, R., et al., "An update on North American Boar stud practices", Theriogenology, vol. 70, pp. 1202-1208, (2008).

Marin, et al., "Metabolic strategy of boar spermatozoa revealed by a metabolomic characterization", FEBS Letters, vol. 554, Issue 3, Nov. 20, 2003, pp. 342-346.

(56) References Cited

OTHER PUBLICATIONS

Martelli, A., et al., "Blood vessel remodeling in pig ovarian follicles during the periovulatory period: an immunohistochemisty and SEM-corrosion casting study", Reproductive Biology and Endocrinology, 2009, 7:72 (2009).
Medrano, A., "Variations in the Proportion of Glycolytic/Non-glycolytic Energy Substrates Modulate Sperm Membrane Integrity and Function in Diluted Boar Samples Stored at 15-17*C", Reproduction in Domestic Animals, vol. 40, pp. 448-453, (2005).
Rath, D., "Production of Piglets Preselected for Sex Following In Vitro Fertilization with X and Y Chromosome-Bearing Spermatozoa Sorted by Flow Cytometry", Theriogenology, vol. 47 pp. 795-800 (1997).
Rath, D., "Low Dose Insemination the the Sow—A Review", Reproduction in Domestic Animals, vol. 37, pp. 201-205 (2002).
Roca, J. et al., "Survival and Fertility f Boar Spermatozoa After Freeze-Thawing in Extender Supplemented With Butylatd Hydroxytoluene", Journal of Andrology, vol. 25, No. 3 pp. 397-405 (2004).
Rodriguez-Gil, J.E., Mammalian Sperm Energy Resources Management and Survival during Conservation in Refrigeration.
Rodriguez-Martinez, H., et al. "Advances in Boar Semen Cryopreservation", Veterinary Medicine International, vol. 2011, Article ID 396181, 5pp. (2011).
Salisbury, G. W, et al., "Substrate-Free Epididymal-Like Bovine Spermatozoa", Journal of Reproduction and Fertility vol. 6, pp. 351-359, (1963).
Spinaci, M., "Sperm Sorting Procedure Induces a Redistribution of Hsp70 but Not Hsp60 and Hsp90 in Boar Spermatozoa", Journal of Andrology, vol. 70, No. 6, pp. 899-907 (2006).
Bergstrom et al., "Effects of Feeder Design, Gender, and Dietary Concentration of Dried Distillers Grains with Solubles on the Growth Perfomance and Carcass Characteristics of Growing-Finishing Pigs" Report of progress 2009, Kansas State University Agricultural Experiment Station and Cooperative Extension Services, 1020.
Knox, Robert V., "The Anatomy & Physiology of Sperm Production in Boars" University of Illinois, Department of Animal Sciences, 2002, pp. 1-11.
Donadeu, Meritxell, "All you ever wanted to know about boar semen." The Pig Site, 2006, http://www.thepigsite.com/articles/1825/all-you-ever-wanted-to-know-about-boar-semen, Retrieved on Jun. 18, 2012.
Roca et al., "Approached Towards Efficient Use of Boar Semen in the Pig Industry" Reprod Dom Anim, 2001, 46, Suppl 2, 79-83.
Rath et al., "Application and Commercialization of Flow Cytometrically Sex-Sorted Semen" Reprod Dom Anim, 2008, 43, Suppl. 2, 338-346.
Rath et al., "Low Dose Insemination Technique in the Pig" IVth Intl Conference on Boar Semen Preservation, Beltsville, Maryland, 2000, pp. 115-118.
Foote, R.H., "Buffers and Extenders: What Do They Do? Why Are They Important?" Proc of the NAAB Tech. Conf. on Artificial Insemination and Reproduction, 62-70 (1984).
Van Wienen et al., "Single Layer Centrifugation with Androcoll-P Can Be Scaled-Up to Process Larger Volumes of Boar Semen." ISRN Veterinary Science, vol. 2011, Article ID 548385, 8 pages.
Rath, D., "Low Dose Insemination in the Sow—A Review" Reprod Dom Anim, 2002, 37, 201-205.
"Guidlines for Uniform Swine Improvement Programs—On-Farm Programs" National Swine Improvement Federation, 1976 revised in 1987 and 1996, http://www.nsif.com/guidel/ONFARM.HTM,pp. 1-9.
Almond, Glen W., "Synchronization of Estrus in Gilts" Proc of the North Carolina Healthy Hogs Seminar, 1997, http://www.ncsu.edu/project/swine_extension/healthyhogs/book1997/almond2.htm, pp. 1-3.
Mathur, P.K., "Effective selection to expedite your genetic progress" Canadian Centre for Swine Improvement Inc., 2002, http://www.ccsi.ca/main.cfm?target_page=select, 7 pages.
Grossfeld et al., "Production of piglets with sexed semen employing a non-surgical insemination technique" Theriogenology, 2005, 63, pp. 2269-2277.
Gil et al., "Morphometry of porcine spermatozoa and its functional significance in relation with the motility parameters in fresh semen" Theriogenology, 2009, 71, 254-263.
Chae et al., "Abnormal gene expression in extraembryonic tissue from cloned porcine embryos" Theriogenology, 2009, 71,323-333.
Rath et al., "In Vitro Production of Sexed Embryos for Gender Preselection: High-Speed Sorting of X-Chromosome Bearing Sperm to Produce Pigs After Embryo Transfer" J. Anim. Sci, 1999, 77, 3346-3352.
Abeydeera et al., "Birth of Piglets Preselected for Gender Following In Vitro Fertilization of In Vitro Matured Pig Oocytes by X and Y Chromosome Bearing Spermatozoa Sorted by High Speed Flow Cytometry" Theriogenology, 1998, 50, 981-988.
Aviles-Lopez et al., "Differences in Tyrosine Phosphorylation in Epididymal and Ejaculated Boar Spermatozoa" Reprod Dom Anim, 2011, 46, 78-161, The 15th Annual Conference of the ESDAR, Abstract P35.
De Ondiz et al., "Immunolocalization Pattern of a-L-fucosidase in Porcine Sperm" Reprod Dom Anim, 2011, 46, 78-161, The 15th Annual Conference of the ESDAR, Abstract P69.
Del Olmo., "The Effect of Butylated Hydroxytoluene on the Functionality of Boar Spermatozoa Undergoing Sex Sorting and Cryopreservation" Reprod Dom Anim, 2011, 46, 78-161, The 15th Annual Conference of the ESDAR, Abstract P73.
Gomis Almendro et al., "Forskolin Improves Vitrification Ability of In Vivo Derived Porcine Zygotes" Reprod Dom Anim, 2011, 46, 78-161, The 15th Annual Conference of the ESDAR, Abstract P109.
Martinez et al., "Effect of Pentoxifylline on Motility Pattern of Fresh Boar Spermatozoa" Reprod Dom Anim, 2011,46, 78-161, The 15th Annual Conference of the ESDAR, Abstract P171.
Maside et al., "Exposure of Porcine in Vitro Matured Oocytes to SYBR 14 and Fluorescence Limits their Developmental Competence" Reprod Dom Anim, 2011, 46, 78-161, The 15th Annual Conference of the ESDAR, Abstract P173.
Matas et al., "Effect of a-L Fucosidase on P-Tyrosine Phosphorylation of Boar Sperm" Reprod Dom Anim, 2011, 46, 78-161, The 15th Annual Conference of the ESDAR, Abstract P175.
Parrilla et al., "Post-Thaw Quality of Boar Semen Frozen at Low Sperm Concentration" Reprod Dom Anim, 2011, 46, 78-161, The 15th Annual Conference of the ESDAR, Abstract P208.
Romero et al., "Preliminary Study on the Roles of a-LFucosidase on Porcine In vitro Fertilization" Reprod Dom Anim, 2011, 46, 78-161, The 15th Annual Conference of the ESDAR, Abstract P234.
Romero et al., "Addition of a-L-Fucosidase to the Porcine In vitro Fertilization Medium Increases Penetration Rates" Reprod Dom Anim, 2011, 46, 78-161, The 15th Annual Conference of the ESDAR, Abstract P235.
Maside et al., "Effects of Hoechst 33342 staining and ultraviolet irradiation on developmental competence of in vitro matured porcine oocytes" Reprod Dom Anim, 2010, vol. 45, pp. 79-102, 2010 Congress of the Spanish Society of Animal Reproduction, Oral Communication 13.
Juarez et al., "The effect of ultra-rapid cooling rate from 17 to 5° C. in inter-boar sperm cryosurvival" Reprod Dom Anim, 2010, vol. 45, pp. 79-102, 2010 Congress of the Spanish Society of Animal Reproduction, abstract P49.
De Ondiz et al., "Sperm a-L-Fucosidase inhibition improved monospermy rate in porcine IVF" Reprod Dom Anim, 2010, vol. 45, pp. 79-102, 2010 Congress of the Spanish Society of Animal Reproduction, abstract P50.
Del Olmo et al., "Influence of seminal plasma and heterodimer PSP-I/PSP-II on the kinematic charges of boar sperm undergoing sex sorting and cryopreservation" Reprod Dom Anim, 2010, vol. 45, pp. 79-102, 2010 Congress of the Spanish Society of Animal Reproduction, abstract P58.
Gomis et al., "Effect of warming in syringe on survival of SOPS-vitrified in vivo derived porcine embryos" Reprod Dom Anim, 2010, vol. 45, pp. 79-102, 2010 Congress of the Spanish Society of Animal Reproduction, abstract P61.

(56) References Cited

OTHER PUBLICATIONS

Sanchez-Osorio et al., "Intraoviductal laparoscopic transfer of porcine somatic cell nuclear transfer embryos" Reprod Dom Anim, 2010, vol. 45, pp. 79-102, 2010 Congress of the Spanish Society of Animal Reproduction, abstract P62.
Del Olmo, "DNA fragmentation in sex-sorted, frozen-thawed boar sperm" Reprod in Domestic Animals, 2011; 46 (supplement 2), 109, 7th International Conference on Boar Semen Preservation, Abstract P54.
Parrilla et al., "Membrane lipid peroxidation in boar spermatozoa subjected to different handlings" Reprod in Domestic Animals, 2011; 46, 89, The 15th Annual Conference of the ESDAR, 0C15.
Maside et al., "Brief exposure of in vitro matured porcine oocytes stained with Hoechst 33342 to ultraviolet irradiation impairs embryo development" Reprod. in Domestic Animals, 2010; 45, 67, 14th Annual Conference of the European Society for Domestic Animal Reproduction, Abstract No. P20.
Bolarin et al., "Reproductive performance of sows returned to estrus after a DUI insemination" Reprod in Domestic Animals, 2010; 45, 79, 14th Annual Conference of the European Society for Domestic Animal Reproduction, Abstract No. P66.
De Ondiz et al., "Sperm a-D-mannosidase and a-L-fucosidase effect on porcine IVF" Reprod in Domestic Animals, 2010; 45, 84, 14th Annual Conference of the European Society for Domestic Animal Reproduction, Abstract No. P85.
De Ondiz et al., "Effect of the presence of glycosidase inhibitors on porcine embryo development in vitro." Reprod in Domestic Animals, 2010; 45, 84, 14th Annual Conference of the European Society for Domestic Animal Reproduction, Abstract No. P86.
Matas et al., "Selection of boar sperm subpopulations by gradients for increasing the in vitro penetration performance" Reprod in Domestic Animals, 2010; 45, 98, 14th Annual Conference of the European Society for Domestic Animal Reproduction, Abstract No. P147.
Parrilla et al., "Effect of intra-oviductal laparoscopic manipulation on future reproductive performance of sows" Reprod in Domestic Animals, 2010; 45, 102, 14th Annual Conference of the European Society for Domestic Animal Reproduction, Abstract No. P162.
Parrilla et al., "Insemination with low or very low number of boar spermatozoa undergoing biotechnological treatments" Reprod Dom Anim, 2011, 46 (Suppl. 3), 60-71,The 15th Annual Conference of the ESDAR, Work Shop ∩10.2.
Garner et al., "Quantification of the X- and Y-Chromosome-Bearing Spermatozoa of Domestic Animals by Flow Cytometry" Biology of Reproduction, 28, 312-321 (1983).
"Methods of Estrus Synchronization for Facilitating Swine Artificial Insemination" Swine Genetics International, http://www.swinegenetics.com/ai_catalog/ai_estrus.html, retrieved Jun. 18, 2012.
Bathgate, et al. "Field fertility of frozen-thawed boar sperm at low doses using non-surgical, deep uterine insemination", Animal Reproduction Science, vol. 103, Issues 3-4, Jan. 2008, pp. 323-335.
Bolarin, A. et al., "Dissimilarities in sows' ovarian status at the insemination time could explain differences in fertility between farms when frozen-thawed semen is used." Theriogenology 2006, 65: 669-680.
Bolarin, et al., "Use of frozen-thawed semen aggravates the summer-autumn infertility of artificially inseminated weaned sows in the Mediterranean region" Journal of Animal Science, 2009, vol. 87, No. 12: 3967-3975.
Fantinati, P., et al., "Laparoscopic insemination technique with low numbers of spermatozoa in superovulated prepuberal gilts for biotechnological application", Theriogenology, Feb. 2005; 63(3): 806-17.
Guthrie, HD, et al., "Impact of storage prior to cryopreservation on plasma membrane function and fertility of boar sperm", Theriogenology, 2005, Jan. 2005; 63 (2): 396-410.
Martinez, E. A., et al., "Deep intrauterine insemination and embryo transfer in pigs", Proceed. of the 6th Int'l Conf. on Pig Reproduction, Univ. Missouri-Columbia, USA, Jun. 2001, pp. 301-311.
Sonesson, A., et al., "Mating schemes for optimum contribution selection with constrained rates of inbreeding", Genetics Selection Evolution, 32 (2000) 231-248.
Woolliams, J.A., et al., "Decision rules and variance of response in breeding schemes", Animal Production, vol. 56, Issue 02, Apr. 1993, pp. 179-186.
Meuwissen, T.H., "Maximizing the response of selection with a predefined rate of inbreeding", Journal of Animal Science, vol. 75 No. 4, Apr. 1997, 934-940.
Vasquez, J.M., et al., "Sex-sorting sperm by flow cytometry in pigs: Issues and perspectives", Theriogenology, vol. 71, pp. 80-88 (2009).
U.S. Office Action dated Mar. 26, 2015, issued in related U.S. Appl. No. 13/840,598.
U.S. Office Action dated Mar. 10, 2016 in related U.S. Appl. No. 13/840,598.
Bathgate et al: "Non-Surgical Deep Intra-Uterine Transfer of In Vitro Produced Porcine Embryos Derived From Sex-Sorted Frozen-Thawed Boar Sperm", Animal Reproduction Science, Feb. 2007, vol. 99, No. 1-2, Apr. 26, 2006 (Apr. 26, 2006), pp. 82-92.
Korean Notification of Provisional Rejection dated Dec. 18, 2015 in related KR Appl. No. 10-2014-14964.
Supplementary European Search Report dated Jan. 22, 2016 in related EP Appl. No. 13800545.9.
Johnson L A et al: "Preselection of Sex of Offspring in Swine for Production: Current Status of the Process and its Application", Theriogenology, vol. 63, No. 2, Jan. 15, 2005, pp. 615-624.
Roca, J, et al. "Approaches Towards Efficient Use of Boar Semen in the Pig Industry.", Reprod Domest Anim. Sep. 2011; vol. 46, Suppl 2, Aug. 26, 2011, pp. 79-83.
Gerrits R J et al: "Perspectives for Artificial Insemination and Genomics to Improve Global Swine Populations", Theriogenology, vol. 63, No. 2, Jan. 15, 2005 (Jan. 15, 2005), pp. 283-299.
D Rath et al: "Application and Commercialization of Flow Cytometrically Sex-Sorted Semen", Reproduction in Domestic Animals, vol. 43, Jul. 1, 2008 (Jul. 1, 2008), pp. 338-346.
Robinson J A B et al: "Impact of Genetic Selection on Management of Boar Replacement", Theriogenology, vol. 63, No. 2, Jan. 15, 2005 (Jan. 15, 2005), pp. 668-678.
Korean Notice of Decision to Grant dated Jan. 3, 2017 in related KR Appl. No. 10-2014-7034384.
U.S. Final Office Action dated Nov. 16, 2016 in related U.S. Appl. No. 14/406,186.
Canadian Examination Report dated Jan. 21, 2016 in related CA Appl. No. 2875058.
New Zealand Examination Report dated Mar. 2, 2016 in related NZ Appl. No. 630356.
Chilean Office Acton dated Mar. 16, 2017 in related CL Appl. No. 3341-2014.
Chilean Office Acton dated Mar. 29, 2017 in related CL Appl. No. 2365-2015.
EP Examination Report dated Jun. 30, 2017 in related EP Appl. No. 13800545.9.
Abdel-Azim G et al: "Genetic Impacts of Using Female-Sorted Semen in Commercial and Nucleus Herds", Journal of Dairy Science, vol. 90, No. 3, Mar. 1, 2007, pp. 1554-1563.
U.S. Notice of Allowance dated Apr. 21, 2017 in related U.S. Appl. No. 14/406,186.
Chinese Examination Report dated May 4, 2016 in related CN Appl. No. 201380029461.5.
Canadian Examination Report dated Jun. 20, 2016 in related CA Appl. No. 2904193.
U.S. Notice of Allowance dated Jul. 21, 2016 in related U.S. Appl. No. 13/840,598.
European Extended Search Report dated Aug. 24, 2016 issued in EP Appl. No. 13877728.9.
Korean Provisional Rejection dated Jul. 29, 2016 issued in KR Appl. No. 10-2014-7034384.
Canadian Office Action dated Aug. 7, 2017 issued in related CA Appl. No. 2,904,193.
Canadian Office Action dated Aug. 4, 2017 issued in related CA Appl. No. 2,875,058.
U.S. Office Action dated Jul. 13, 2015, issued in related U.S. Appl. No. 13/840,598.

(56) References Cited

OTHER PUBLICATIONS

NZ Office Action dated Aug. 21, 2015, issued in related application No. 630356.
Chilean Office Action dated Oct. 13, 2017 issued in related CL Appl. No. 201502365.
Chinese Patent Examination Report dated Sep. 24, 2015 in related CN Appl. No. 201380029461.5.
U.S. Final Office Action dated Feb. 11, 2016 in related U.S. Appl. No. 14/090,979.
U.S. Office Action dated Jun. 28, 2016 in related U.S. Appl. No. 14/090,979.
U.S. Final Office Action dated Dec. 19, 2016 in related U.S. Appl. No. 14/090,979.
U.S. Notice of Allowance dated Oct. 6, 2017 in related U.S. Appl. No. 14/090,979.
Chilean Office Acton dated Dec. 28, 2017 in related CL Appl. No. 3341-2014.
Canadian Requisition dated Jun. 26, 2018 in related CA Application No. 2,904,193.
Chinese Office Action dated Jul. 17, 2018 in related CN Application No. 201380074208.1.
Canadian Requisition dated Jul. 9, 2018 issued in related CA Appl. No. 2,875,058.
U.S. Notice of Allowance dated Sep. 4, 2018 issued in related U.S. Appl. No. 15/655,663.
European Invitation pursuant to Rule 137(4) dated Apr. 16, 2018 issued in EP Appl. No. 13877728.9.
Mexican Examination Report dated Mar. 13, 2018 issued in related MX Appl. No. MX/a/2014/015000.
Mexican Examination Report dated Mar. 13, 2018 issued in related MX Appl. No. MX/a/2014/012648.
U.S. Office Action dated Mar. 22, 2018 in related U.S. Appl. No. 15/655,663.
Day et al. "Birth of Piglets Preselected for Gender Following In Vitro Fertilization of In Vitro Matured Pig Oocytes by X and Y Bearing Spermatozoa Sorted by High Speed Flow Cytometry." Theriogenology 49(1):360, 1998.
Merks. "Genetic Improvement at the Commercial Level Compared to Genetic Progress at the Nucleus Level." Printout from http://www.nsif.com/conferences/2001/merks1.htm, pp. 1-10, 2001.

* cited by examiner

METHODS FOR USE OF SEX SORTED SEMEN TO IMPROVE GENETIC MANAGEMENT IN SWINE

This application is a continuation of U.S. application Ser. No. 14/090,979, filed on Nov. 26, 2013, which a continuation in part of U.S. application Ser. No. 13/840,598, filed Mar. 15, 2013, now U.S. Pat. No. 9,433,195, issued Sep. 6, 2016, which claims priority to U.S. Application No. 61/656,446, filed on Jun. 6, 2012.

FIELD OF THE INVENTION

The invention relates to methods of using sex sorted semen from pure line boars of a swine line in matings to increase the genetic merit of swine at the level of commercial pig production. The improvement of genetic management of the line is the result of 1) increase of the genetic progress in the line and/or 2) improvement of the genetic dissemination (i.e., genetic merit of commercial product is closer to genetic merit at the genetic nucleus).

BACKGROUND

Swine production today can be represented by a multi-level pyramid, with certain offspring at each level used in the next lower level for breeding. The top level of the pyramid is the genetic nucleus (GN). The next levels from top to bottom are generally the daughter nucleus (DN), the multiplier, or multiplication unit, and finally the commercial level, generally comprising commercial farms where slaughter pigs are being produced, respectively.

Typically, genetic progress of a line takes place in the pure line population at the genetic nucleus. The GN animals will have relatives at lower levels of the pyramid, pure bred as well as crossbred. Trait data collected from these relatives contribute to the estimation of the genetic merit of GN animals. Within a line at the GN, once selected, parents that produce the next generation are in general randomly mated with one another, while avoiding matings between closely related individuals, with the goal of increasing the genetic merit of the next generation. An increase in the genetic merit of the next generation constitutes genetic progress. An increase in genetic merit, in this context, means that for a given trait or set of traits, the individuals in the successive generation will express the desired trait or set of traits more strongly than their parents. With respect to undesirable traits, an increase in genetic merit means the individuals in the successive generation will express the trait or set of traits less strongly than their parents.

Genetic change, including desirable genetic change (i.e., genetic progress per year), ("dG") can be measured as the difference between the average genetic level of all progeny born in one year and all progeny born the following year. The difference is the result of selected parents having higher genetic merit than the average genetic merit of all the selection candidates (the animals available for selection). In ideal conditions, this depends upon the heritability ($h^2$) of the trait and the difference between the average performance of selected parents and that of selection candidates. The heritability of a trait ($h^2$) is the proportion of observable differences (phenotypic variance, $\sigma^1_P$) in a trait between individuals within a population that is due to additive genetic (A), as opposed to environmental (E), differences ($h^2 = \sigma^2_A/\sigma^2_P = \sigma^2_A/(\sigma^2_A + \sigma^2_E)$). The difference between the average performance of selected parents and that of all selection candidates (of which the selected parents are a subset) is also known as the selection differential.

The genetic progress per year is the result of genetic superiority of selected males and of selected females. This is expressed in the following equation:

$$dG = \{(R_{IH}*i)_{males} + (R_{IH}*i)_{females}\} * \sigma_H / (L_{males} + L_{females}),$$

Where, R=the accuracy of selection, i=the selection intensity, $\sigma_H$=genetic variation and L=generation interval, for male or female parents.

H=breeding goal that combines genetic merit (g) of the traits (1 to m) that need to be produced weighted by the economic values (v) of the traits ($H = v_1 g_1 + v_2 g_2 + \ldots + v_m g_m$). The economic value is positive if selection is for larger phenotypic values and negative if selection is for smaller phenotypic values.

I=an index that combines all the trait information on the individual and its relatives and is the best estimate of the value of H for the individual.

Selection is more effective when non-genetic effects are removed (e.g. by comparing each performance record to the average of the contemporary group) and when information from relatives is used in addition to that of the animal itself. This is achieved through the computation of estimated breeding values (EBVs) using for instance multiple trait BLUP methods. Environmental factors such as HYS (herd-year-season) are in the model to correct for environmental effects and simultaneously information from relatives is included through the use of the relationship matrix. More trait information from more relatives results in a higher accuracy ($R_{IH}$) of the EBV.

In a large population, the selection intensity depends upon how many animals are tested and how many are selected— the lower the proportion selected the higher the selection intensity and the larger the genetic progress, all else being equal. Thus, in order to maximize genetic progress, one should rank all tested animals based on the EBV and then select the minimum number of top boars and sows required to maintain the line, breed and/or herd size and to avoid inbreeding problems. This ensures that the average EBV of selected animals is substantially higher than the average EBV of all animals tested. In particular through the use of artificial insemination (AI), one needs to select fewer boars than gilts and the selection intensity for males is higher than for females.

The generation interval for males (or females) is the average age of male parents (or female parents) when progeny are born. In general sows produce more than one litter at the GN and the L for females tends to be larger than the L for males.

The annual rate of genetic progress depends on the generation interval and on the superiority of the parent's EBVs compared to that of the selection candidates. In general, males contribute more to the genetic progress per year than the females.

Examples of important traits in the swine industry are feed efficiency, i.e., a measure of an animal's efficiency in converting feed mass into increased body mass (also known as feed conversion or feed to gain ratio), and average daily gain, i.e., the average daily weight gain for an animal. Traits are measured in different units (e.g., number of pigs, pounds per day, inches, etc.), are not of equal economic importance in all global markets, and are not genetically influenced to the same degree (i.e., different heritability coefficients). Generally speaking, production traits such as feed efficiency and average daily gain have high heritability. In contrast, reproductive traits such as fertility and litter size generally have low heritability.

There is a need in the swine industry to increase the rate of genetic progress in lines as well as to lower operational costs on breeding and commercial swine farms.

SUMMARY OF THE INVENTION

Certain embodiments of the invention comprise a method of increasing genetic merit of swine comprising the steps of establishing a plurality of mating subtypes for a line; determining a percentage of progeny that are male for each of the mating subtypes, or a percentage of progeny that are female for each of the mating subtypes, that would result, relative to a control, in an increase in genetic merit; sorting a sperm cell sample from a male swine in one of the mating subtypes into one or more subpopulations of sperm cells, wherein a majority of sperm cells in a subpopulation of sperm cells bear X chromosomes or Y chromosomes; inseminating one or more female swine in the one of the mating subtypes with the subpopulation of sperm cells to achieve the percentage of progeny that are male or the percentage of progeny that are female determined to increase genetic merit relative to a control; and producing progeny from the one or more female swine. In a further embodiment, the percentage of progeny that are male for each of the mating subtypes, or the percentage of progeny that are female for each of the mating subtypes, results in an increase in genetic merit and no increase in inbreeding in the line relative to a control. In a further embodiment, the step of inseminating may be replaced by a step of fertilizing, either in vivo or in vitro, one or more eggs from one or more female swine in the one of the mating subtypes with the subpopulation of sperm cells to achieve the percentage of progeny that are male, or the percentage of progeny that are female, determined to increase genetic merit relative to the control. In certain embodiments of the invention, the line, the male, the one or more female, and/or the progeny, may belong to or be members of a genetic nucleus, a daughter nucleus or a multiplier. In other embodiments of the invention, any or all of the aforementioned steps may be performed as part of a breeding program. It should be understood that certain embodiments of the invention comprise one or more of the aforementioned steps.

It should be understood that in certain embodiments of the invention, at least approximately 60%, 65%, 70%, 75%, 80%, 85%, 90%, 95%, 96%, 97%, 98%, 99% or 100% of sperm cells in the subpopulation of sperm cells bear X chromosomes or Y chromosomes.

In certain embodiments of the invention, genetic merit of a swine or a line may be a function of, based on, or determined by, quantitative or genomic EBV. In other embodiments of the invention, genetic merit may be a function of, based on, or determined by, one or more traits, including but not limited to fertility, litter size, milk production, feed efficiency, average daily gain and carcass lean, as well as genetic markers for such traits. In a further embodiment, genetic merit may be a function of, based on, or determined by, the ability of sperm cells to be sex sorted and/or frozen based on the sperm cells viability, fertility, and/or motility after sorting and/or freezing, as well as a genetic marker for such a trait.

In certain embodiments of the invention, a line may comprise a sire line or a dam line In certain aspects of the invention, a line may comprise a sire line and the percentage of progeny that are male for each of the mating subtypes, or the percentage of progeny that are female for each of the mating subtypes, determined to increase genetic merit of the line relative to a control, results in a percentage of progeny that are male for the line that is between approximately 10 to 35% or 15 to 30%. In other aspects, a line may comprise a dam line and the percentage of progeny that are male for each of the mating subtypes, or the percentage of progeny that are female for each of the mating subtypes, determined to increase genetic merit of the line relative to a control, results in a percentage of progeny that are male for the line that is between approximately 5 to 30% or 10 to 25%. In yet further aspects, the percentage of progeny that are male for each of the mating subtypes, or the percentage of progeny that are female for each of the mating subtypes may be between approximately 0 to 10% or between approximately 90 to 100% and the produced progeny may be members of a daughter nucleus or a multiplier.

In certain embodiments of the invention, approximately 50% of progeny are male in the control. In other embodiments, all female swine to be mated are inseminated with unsorted semen samples in the control.

In some aspects of the inventions, a category or class of male swine in one or more of the mating subtypes may be defined by one or more characteristics, including genetic merit or age. In other aspects, a category or class of female swine in one or more of the mating subtypes may be defined by one or more characteristics, including genetic merit or parity. In some embodiments, each of the mating subtypes in the plurality of mating subtypes may comprise only one male swine and/or only one female swine from the line. In some embodiments of the invention, a mating subtype may be comprised of one or more subgroups and/or one or more female subgroups, wherein a subgroup is defined or based on one or more criteria, including but not limited to, function in the production pyramid, age, parity, genetic merit (e.g., EBV) and genetic markers or mutations. Some embodiments of the invention comprise the step of classifying or splitting males and/or females available for mating into a plurality of subgroups, wherein the subgroups are defined by, or based on, one or more criteria including but not limited to, function in the production pyramid, age, parity, genetic merit (e.g., EBV) and genetic markers or mutations. In a further embodiment, the aforementioned step of classifying or splitting is performed in a line or as part of a breeding program or as a step in creating a mating plan for a line. In certain embodiments, a male subgroup is defined by, or based on, one or more criteria including but not limited to, function in the production pyramid, age, genetic merit (e.g., EBV) and genetic markers or mutations. In certain embodiments, a female subgroup is defined by, or based on, one or more criteria including but not limited to, function in the production pyramid, parity, age, genetic merit (e.g., EBV) and genetic markers or mutations. In some embodiments of the invention, one or more male subgroups can cover one or more males. In other embodiments of the invention, one or more female subgroups can cover one or more females.

It should be understood that in certain embodiments of the invention, the percentages of male and/or female progeny that increase genetic merit may be determined using a stochastic or a deterministic method, or a combination thereof.

In certain embodiments of the invention, genetic merit of a swine or a line may be a function of, based on, or determined by, EBV. In other embodiments of the invention, genetic merit may be a function of, based on, or determined by, one or more traits, including but not limited to fertility, litter size, milk production, feed efficiency, average daily gain and carcass lean, as well as genetic markers for such traits. In a further embodiment, genetic merit may be a function of, based on, or determined by, the ability of sperm cells to be sex sorted and/or frozen based on the sperm cells viability, fertility, and/or motility after sorting and/or freezing, as well as a genetic marker for such a trait. In certain embodiments of the invention, genetic merit of a swine or a line may be assessed by genotyping a swine or an embryo.

In certain embodiments of the invention, sex sorted semen may comprise sex sorted sperm cells, or sex sorted sperm cells and one or more other components of an ejaculate. In other embodiments, a sex sorted sperm cell sample may comprise a sperm cell sample in which either X- or Y-bearing sperm cells in the sample have been rendered incapable of fertilization by, for example, killing. In other embodiments, the process of sex sorting a sperm cell sample or a semen sample includes any process in which either X- or Y-bearing sperm cells in the sample are identified and rendered incapable of fertilization.

Other aspects of the invention encompass inseminating a female swine from said line or breed with sex sorted sperm cells using a deep intrauterine catheter or a needle inserted through a membrane of said female swine. Some of these embodiments encompass known surgical and non-surgical techniques that can be used to place sperm cells into a female swine's reproductive tract, including laparotomy (surgical procedure involving a large incision through the abdominal wall to gain access into the abdominal cavity). This embodiment contemplates inseminating female swine using $1 \times 10^9$ or less total sperm cells.

In other embodiments, a deep intrauterine catheter can be employed to administer a sperm cell sample into distal portions of a female swine's reproductive tract such as one or more uterine horns or one or more utero-tubal junctions. In another aspect of the invention, the deep intrauterine catheter is comprised of an outer tube or sheath and an inner flexible probe. In a further aspect of the invention, the flexible inner probe comprises a flexible inner duct through which fluids or cells can pass. In certain embodiments of the invention, the outer tube and inner flexible probe can be made of a plastic, and in other embodiments, they may be made of metal configured to be flexible such as in a coil or spring configuration. In a further embodiment, the deep intrauterine catheter comprises a video camera or scope for visualizing the location of the distal portion of the deep intrauterine catheter within a female swine's reproductive tract. In an alternative embodiment, the deep intrauterine catheter can be visualized within the female swine's reproductive tract using radiography or fluoroscopy. In another embodiment of the invention, a deep intrauterine catheter can be used to insert or withdraw embryos or zygotes from the distal portions of a female swine's reproductive tract such as from one or more uterine horns or from one or more utero-tubal junction.

With respect to insemination with a deep intrauterine catheter, it is contemplated that a dose of $1 \times 10^9$ sperm cells or less is administered to a female swine. Such sperm cells may be sex sorted sperm cells. In one embodiment of the invention a dose of sex sorted sperm cells (for instance $600 \times 10^6$, but may be more, or as little as $10 \times 10^6$ if placed in the optimal location at the optimal time of estrus) is administered into one or both uterine horns (e.g., $300 \times 10^6$ sperm cells into each horn) of a female swine by deep intrauterine catheter. In other embodiments, doses can vary in the range of or anywhere in between about $300 \times 10^6$, about $150 \times 10^6$, about $140 \times 10^6$, about $100 \times 10^6$, about $70 \times 10^6$, about $50 \times 10^6$, or about $5 \times 10^6$ sex sorted sperm cells or less and can be administered into one or both uterine horns of a female swine.

The aforementioned doses can be administered in various volumes, including but not limited to 5 ml for every $150 \times 10^6$ sperm cells, or the same number of cells in a volume in the range of 5 ml, 10 ml, 15 ml, 20 ml, 25 ml, 30 ml or 100 ml, or somewhere between 5-10 ml, 10-20 ml, 20-30 ml, 30-40 ml, 40-50 ml, 50-60 ml, 60-70 ml, 70-80 ml, 80-90 ml or 90-100 ml.

The sex sorted sperm cells for use in any embodiment of the invention can be cryopreserved and then thawed, or alternatively fresh (i.e., never frozen) sex sorted sperm cells can be utilized. The aforementioned doses may also be administered into one or more utero-tubal junctions of a female swine.

This embodiment of the invention also encompasses the use of a laparoscope to visualize insertion of a needle through a membrane of a female swine for administering a sex sorted sperm cell sample. Both the needle used for injecting the sperm cell sample and the laparoscope, as well as manipulating instruments such as forceps, can be inserted into the abdomen of a female swine through small incisions typical of laparoscopic procedures. The invention also encompasses the injection of a sperm cell sample in one or more locations within the female reproductive tract. By way of example only, the sperm cell sample can be injected in one or more locations within the uterus of a female swine, including one or more uterine horns, oviducts, ampulla, isthmus or utero-tubal junction. In another embodiment of the invention, embryos or zygotes can be inserted or withdrawn from a female swine's reproductive tract via laparoscopy.

With respect to insemination via laparoscopy, it is contemplated that a dose of $1 \times 10^9$ sperm cells or less is administered to a female swine. Such sperm cells may be sex sorted sperm cells. In one embodiment of the invention a dose of about $500 \times 10^6$ sex sorted sperm cells or less can be injected into one or both oviducts (e.g., $250 \times 10^6$ sperm cells in each oviduct) of a female swine by laparoscopy; in other embodiments, doses in the range of or anywhere in between about $10 \times 10^6$, about $5 \times 10^6$, about $3 \times 10^6$, about $2.0 \times 10^6$, about $1.2 \times 10^6$, about $1 \times 10^6$, or $0.6 \times 10^6$ sex sorted sperm cells or less can be injected into one or both oviducts of a female swine.

In a further embodiment, sex sorted sperm cells can be injected into specific regions of the oviduct, including but not limited to the isthmus, the ampulla and/or the utero-tubal junction. In certain embodiments, a dose in the range of or anywhere in between about $5 \times 10^6$, about $2 \times 10^6$, about $1 \times 10^6$, about $600 \times 10^3$, about $500 \times 10^3$, about $300 \times 10^3$, or about $150 \times 10^3$ sex sorted sperm cells or less, can be injected into one or more regions of the oviduct, either unilaterally or bilaterally.

In a further embodiment with respect to insemination via laparoscopy, sex sorted sperm cells can be injected at various sites in the oviduct using doses in the range of or anywhere in between the about $500 \times 10^3$ sex sorted sperm cells injected into each ampulla with about $1 \times 10^6$ sex sorted sperm cells injected into each utero-tubal junction; or a dose of about $1 \times 10^6$ sex sorted sperm cells injected into each ampulla with about $2 \times 10^6$ sex sorted sperm cells injected into each utero-tubal junction; or a dose of about $5 \times 10^5$ sex sorted sperm cells injected into each ampulla with about $2 \times 10^6$ sex sorted sperm cells injected into each utero-tubal junction; or a dose of about $5 \times 10^5$ sex sorted sperm cells injected into each ampulla with about $1 \times 10^6$ sex sorted sperm cells injected into each utero-tubal junction. The aforementioned doses can be contained in various volumes, by way of example, 100 µl for every 1×10⁶ million sperm cells, or the same number of sperm in one of the following or in any volume between: 50 µl, 100 µl, 200 µl, 300 µl, 400 µl or 500 µl.

Another aspect of the invention comprises synchronizing estrus and/or inducing timed ovulation in a female swine that is to be inseminated using the embodiments disclosed herein by administering one or more hormone or hormone analogs to the female swine. In one embodiment, the one or more hormone or hormone analogs comprises PG600 (comprising pregnant mare's serum gonadotropin ["PMSG"] and human chorionic gonadotropin ["hCG"]; Intervet), OvuGel (triptorelin acetate in a slow release formula via an intravaginal delivery system; Gel Med Sciences, Inc.), equine chorionic gonadotropin ("eCG"), hCG, progestin, altrenogest or regumate.

In a further embodiment of the invention, said one or more hormone or hormone analogs is administered by a programmable device placed in the reproductive tract of said female swine. The programmable device contemplated herein is able to release said one or more hormone or hormone analogs in a time released fashion without the breeder having to monitor the device or provide any input other than programming the initial parameters for release of said one or more hormone or hormone analog. In another embodiment of the invention, estrus synchronization/timed ovulation can be induced in a female swine by administering 1250 to 1500 IU of eCG and then 750 IU of hCG 72 to 80 hours later. In another embodiment, estrus can be induced in a female swine by administering 400 to 2000 IU of PMSG and then 500 to 1000 IU of hCG is administered 72 to 83 hours later.

Other embodiments further contemplate detecting ovulation in a female swine by examining said female swine's follicles. In a particular embodiment of the invention, said female swine's follicles are examined using ultrasound. In a further embodiment, said female swine's ovaries are examined by transrectal ultrasound every 3-5 hours beginning 25-35 hours after hCG injection for the presence of pre-ovulatory follicles. In a further embodiment of the invention, female swine showing multiple pre-ovulatory follicles are selected for insemination 2-3 hours after ultrasound.

DETAILED DESCRIPTION OF THE INVENTION

Figure 1:
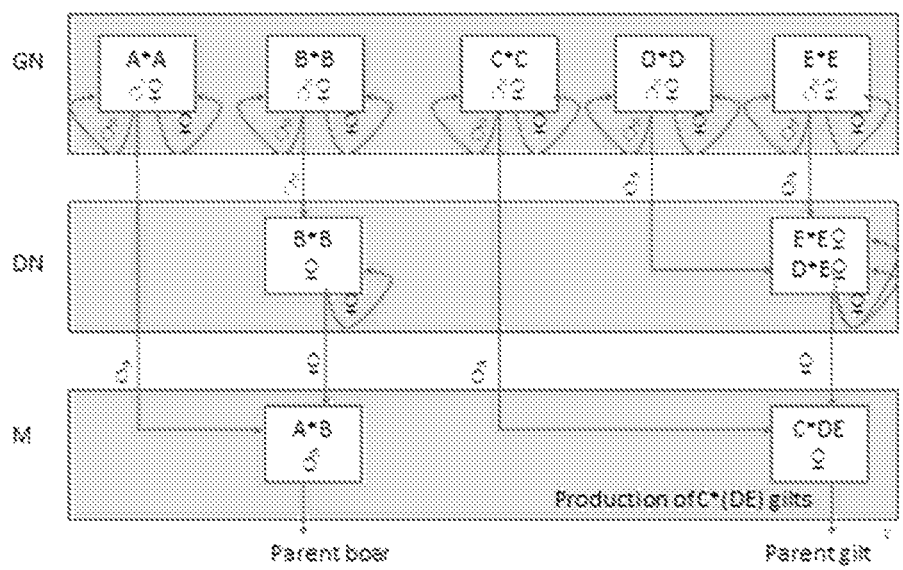
FIG. 1 shows an example of a production pyramid for the production of crossbred parent boars and parent gilts.

The methods disclosed herein increase the genetic merit of swine at the commercial level by increasing the rate of genetic progress of a line and/or reducing the genetic lag between the GN and commercial production while making multiplication more cost effective and/or profitable.

"Line" as used herein refers to swine having a common origin and similar identifying characteristics. "Pure line" as used herein is equivalent to "line," and may be used below in order to distinguish a pure bred individual or mating from a crossbred individual or mating.

"Breeding program" as used herein comprises one or more line development programs.

"Commercial swine" refers to swine slaughtered for their meat for commercial sale or sows producing swine for their meat for commercial sale.

"Commercial farm" as used herein refers to a facility for housing commercial swine.

"Multiplier," or "multiplication unit," as used herein refers to one or more populations of male and female swine, comprising one or more lines that are part of a multiplication program for increasing the number of individuals with increasing genetic merit, with individuals being pure line or crossbred products used as parents, grandparents or great grandparents of commercial swine.

"Daughter nucleus" as used herein refers to one or more populations of male and female swine used for pure line multiplication.

"Genetic nucleus" as used herein refers to one or more populations of male and female swine, comprising one or more lines that are part of a breeding program for increasing the genetic merit of the one or more lines, and may include, or comprise the functions of, a daughter nucleus.

"Mating subtype" as used herein refers to a defined class of potential mating between: 1) a defined category, class or type of male and available females; 2) available males and a defined category, class or type of female; or 3) a defined category, class or type of male and a defined category, class or type of female.

"Sire line" as used herein refers to a line that contributes to the production of parent boars used on commercial farms.

"Dam line" as used herein refers to a line that contributes to the production of parent gilts/sows used on commercial farms.

At every level in the swine production pyramid, for each mating type, from genetic nucleus ("GN") to commercial production, one has males (boars and/or their semen) and females (gilts/sows and/or their eggs) to choose from for the production of progeny.

At the GN, pure line matings take place, males and females are being produced, and the best tested males and females are used to produce the next generation. In general (but not always), only GN males (or their semen) are used for genetic dissemination to lower levels of the pyramid (daughter nucleus ["DN"] or multiplier ["M"]).

Generally, the grandparents of slaughter pigs are produced at the DN and parents of the slaughter pigs are produced at the M level. In the example given in FIG. 1, only one of the two sexes needs to be produced at the DN or M level for one mating type. At the commercial level parent boars and parent gilts/sows produce the slaughter pigs. The split between levels of the production pyramid depends on specific features of a production system. In a closed herd commercial structure, several levels can be found within one farm (structure). But in terms of matings, one still generally deals with the mating types as described in FIG. 1.

Referring to FIG. 1, each letter—"A," "B," "C," "D" and "E"—represents a pure line where A and B are sire lines and C, D and E are dam lines. In each square block of FIG. 1, a mating type or types (for instance, "A*A," "D*E," "C*DE," etc.) and the desired sex of the piglets ("♂" and/or "♀") are shown. The details of a multiplication structure (DN and M, wherein M generally comprises a parent boar M and a parent gilt M) depend on the breeding company (large or small), its customers (large or small) and the final product (3, 4 or 5-way cross). FIG. 1 gives one example of a production pyramid. One sees sire lines (e.g., B) producing gilts and dam lines (e.g., C) producing boars. For each of the lines, the most superior tested boars are moved to an AI station and their semen used: 1) for pure line matings at the GN, producing male AND female desired progeny and 2) for pure line matings or crossbred matings at DN/M producing male OR female desired progeny.

An increase of genetic progress in the GN generally involves the production, testing and selection of boars and gilts. In the traditional situation (i.e., use of unsorted semen), there are effectively two selection pathways: sires to produce sires and dams and dams to produce sires and dams. The use of sex sorted semen creates an opportunity to use four selection pathways (i.e., sires to produce sires ["SS"], sires to produce dams ["SD"], dams to produce sires ["DS"], and dams to produce dams ["DD"]) and to increase the genetic merit and rate of genetic progress at the commercial level. The rate of genetic progress per year in a line at the GN is a function of accuracy of selection, selection intensity, genetic variation and generation interval:

$$dG = \{(R^*i)_{SS} + (R^*i)_{SD} + (R^*i)_{DS} + (R^*i)_{DD}\} * \sigma_H/(L_{SS} + L_{SD} + L_{DS} + L_{DD}),$$

where,
R is the accuracy of selection with in general $R_{SS} = R_{SD} \geq R_{DS} = R_{DD}$
L is the generation interval with $L_{SS}$ the average of boars when male progeny are born, $L_{SD}$ the average age of boars when female progeny are born, $L_{DS}$ the average age of sows when male progeny are born and $L_{DD}$ the average age of sows when female progeny are born.
i' is the selection intensity for each of the four pathways.

With four selection pathways available, one has the choice to select which particular male parent or which particular female parent within a population produces male offspring, and which particular male parent or which particular female parent within a population produces female offspring. The concept of "Precision Breeding," as disclosed herein, allows one to pinpoint the best male, and female parents for the production of a particular gender in order to increase the genetic merit and rate of genetic progress at the commercial level through a mating, testing and selection plan using sex sorted semen. The use of this new breeding approach is termed "Precision Breeding."

A core principle underlying Precision Breeding is that for each mating type, as illustrated in FIG. 1, one has males (boars and/or their semen) and females (gilts/sows and/or their eggs) at the GN and the DN/M available for the production of male and/or female progeny. In order to generate a mating plan for a mating type using Precision Breeding, the males and/or females available for mating are first classified or "split" into subgroups based on certain criteria including, but not limited to, function in the production pyramid, age, parity, genetic merit (e.g., EBV) and/or genetic markers or mutations.

TABLE 1

|  |  | Male subgroups[b] | | | | |
|---|---|---|---|---|---|---|
|  |  | 1 | 2 | 3 | 4 | 5 |
|  |  | % of male progeny[a] | | | | |
| Female sub | 1 | P11 | P12 | P13 | P14 | P15 |
|  | 2 | P21 | P22 | P23 | P24 | P25 |
| groups[c] | 3 | P31 | P32 | P33 | P34 | P35 |
|  | 4 | P41 | P42 | P43 | P44 | P45 |

TABLE 1-continued

[a]The percentage of male progeny in litters (Pij) produced by a subgroup of male and a subgroup of female parents.
[b]The males available for mating are split into 5 subgroups based on age and/or merit.
[c]The females available for mating are split into 4 subgroups based on age and/or merit.

In the example in Table 1, we have defined five subgroups for the males and four subgroups for the females. For each $i^{th}$ male and $j^{th}$ female subgroup combination (each subgroup combination represents a mating subtype) one can determine the percentage of male progeny ($P_{ij}$) and female progeny ($Q_{ij}$) that results in the largest increase in genetic merit. $P_{ij} + Q_{ij} = 100$. $P_{ij}$ can range from 0 to 100.

The males might be split into 'a' age subgroups and within each age subgroup, split into 'b' additional subgroups based on their EBV. For example, the sows might be split into 'p' parity subgroups at the GN and 'q' parity subgroups at DN/M. Furthermore, within each parity subgroup, sows might be split into 'n' additional subgroups based on, for example, their EBV. This will result in 'ab' subgroups for males and '(p+q)n' subgroups for females giving a total of 'ab(p+q)n' mating subtypes for a specific mating type illustrated in FIG. 1.

In one embodiment of Precision Breeding, each male and each female is treated as a mating subgroup and the percentage of male progeny that yields the largest increase in genetic merit is determined for each potential mating.

This general principle can be applied in different situations and with different objectives. Generally, in order to implement Precision Breeding technology in a genetic improvement program, there are a number of steps that may be performed:

One step is to determine the resources available for development of lines and multiplication. Relevant resources include, but are not limited to, the number of sow places at the GN and DN/M, the performance test capacity at the GN and DN, the number of crossbred progeny to test at commercial farms per GN boar (pure line boars used for breeding at the GN), and the budget.

Another step is to define a genetic improvement program that does not use Precision Breeding technology. In certain embodiments of the invention, a genetic improvement program may be designed to yield maximum genetic progress for a given level of inbreeding and/or as a function of available resources. Major elements include, but are not limited to, the maximum parity, the number of GN boars selected for breeding per year, the period (number of days) during which a selected GN boar is used for breeding, the breeding goal and phenotype data collection.

A further step is to estimate the genetic improvement per year with a line development program using deterministic and/or stochastic methods.

An additional step is to define a line development program that uses Precision Breeding and sex sorted semen technology. In certain embodiments of the invention, in addition to defining the line development program along conventional parameters, this will comprise splitting the males and females available for mating into subgroups. For example, females can be split into 'n' parity subgroups and into 'p' EBV subgroups within each parity subgroup. This results in 'n*p' female subgroups. Males can be split into 'a' age subgroups and into 'b' EBV subgroups within each age subgroup. This results in 'a*b' male subgroups. A mating plan can then be developed using a matrix of the 'np'*'ab' mating subtypes.

Another step is to develop a mating plan for a line development program that uses Precision Breeding technology. Generally, the goal of such a mating plan will be to increase genetic progress without increasing inbreeding in the line, relative to a mating plan for a line development program in which Precision Breeding technology is not used (i.e., a control). With respect to a mating plan for a line development program that uses Precision Breeding technology, a percentage, or a range of percentages, of progeny that are male or female for each mating subtype that results in an increase in genetic progress, and no increase in inbreeding, relative to a control can be determined using stochastic and/or deterministic methods. In certain embodiments of the invention, the percentage of progeny that are male or female for each mating subtype that results in the maximum increase in genetic progress, and no increase in inbreeding, relative to a control can be determined using stochastic and/or deterministic methods.

An additional step that may be performed in a line development program that uses Precision Breeding technology is to inseminate one or more females in a mating subtype with sex sorted semen to achieve a percentage of progeny that are male or female as determined in a mating plan. For this purpose, the sex sorted semen may be obtained from one or more males in the same mating subtype as the females.

In certain embodiments of the invention, a control may comprise the same individuals as those used in a mating plan for a line development program that uses Precision Breeding technology and may be simulated using any method known in the art. Additionally, a line development program that uses Precision Breeding technology and a line development program for a control may be defined identically except for those features found only in a line development program that uses Precision Breeding technology.

A condition that may be assumed for both the mating plan for a line development program that uses Precision Breeding technology and the control is that each female at any point in time can only be used in combination with one male, unless mixed semen is being used. With respect to the control, it may further be assumed that females selected as parents are randomly mated with available males except that matings between closely related individuals such as full-siblings and half-siblings are avoided, and that each litter has on average a 50/50 split between male and female progeny. Alternatively, with respect to the mating plan for a line development program that uses Precision Breeding technology, it may be assumed that each mating subtype will have a target for production of a certain average percentage of males or females, ranging from 0 to 100% and for each litter in general a target of 0, 50 or 100%.

In certain embodiments of the invention, a mating plan for a line development program that uses Precision Breeding technology may simply comprise a framework or general guidelines that are derived from the specific target percentages determined for each mating subtype. For example, a general guideline may be that each generation comprise a certain percentage of males overall or that young, high EBV parents should preferentially produce males. A framework or general guidelines will generally be implemented to increase genetic progress, without an increase in inbreeding, relative to a control.

Another step is to include matings at the DN/M level in a mating plan with optimal percentages of male or female pigs in order to make optimal use of the semen production capacity per boar and to use the most superior boars to contribute to genetic improvement and control of inbreeding as well as genetic dissemination to ultimately the commercial level.

As an alternative, or in addition, to testing or assessing progeny phenotypically, in certain embodiments of the invention, genomic selection or mutation assisted selection may be implemented. With respect to mutation assisted selection, GN breeding animals will carry a known number of favourable mutations and certain individuals may become very important for a genetic improvement program. For example, if there are three mutations of interest and the frequency of the favourable allele is 0.5, only 1.56% of the animals will be found to be homozygous for all three favourable alleles. If the number of identified favourable mutations increases and/or the frequencies of favourable alleles decreases, the percentage of individuals with the ideal genotype will drop.

Application of Optimum Genetic Contribution Theory in Precision Breeding

Intensive selection in species such as swine increases the risk of loss of genetic diversity through an increase of inbreeding and relationships between animals in a population, resulting in a higher percentage of detrimental recessive genes in the homozygous state and in inbreeding depression. Inbreeding is generally not problematic for existing breeding programs since they take inbreeding into consideration. Amongst these existing breeding programs, inbreeding is generally restricted to a less than 1% increase per generation.

Initially inbreeding was controlled by restricting the number of full- and half-siblings produced and/or selected for and by avoiding matings between full- and half-siblings. Currently, most breeding programs limit inbreeding by implementing rules based on optimum genetic contribution theory ("OGC"). OGC maximizes genetic progress while constraining the rate of inbreeding or the relationships among selected candidates (see Woolliams, J. and Meuwissen, T., 1993, Decision rules and variance of response in breeding schemes, Anim. Prod. 56:179-186; and Meuwissen, T., 1997, Maximizing the response of selection with a predefined rate of inbreeding. J. Anim. Sci. 75:934-940).

Application of OGC in breeding programs generally comprises two steps:
1. Choose the selected parents from the selection candidates and assign genetic contributions to the next generation for each selected candidate.
2. Develop a mating plan involving the selected candidates that minimizes average inbreeding in the next generation.

In swine it works as follows:

A certain number of male and female progeny are produced per generation or per period (for instance per week).

After the performance test selection decisions need to be made. Use of the OGC theory results in the calculation of the optimum genetic contribution for each of the performance tested individuals. Individuals with a calculated contribution below a certain threshold (different threshold for males and females) are culled and the selected individuals are then available for breeding.

In each period a number of males and females are available for breeding and algorithms can be used to develop the mating plan resulting in minimal average inbreeding.

There are several commercial software packages available to implement the above concepts. For use of OGC, packages such as GENCONT, EVA (Nordgen) and TGRM™ (X'Prime) are available, and for mating design, use of a simulated annealing algorithm (Sonesson, A. and Meuwissen, T., 2000, Mating schemes for optimum contribution selection with constrained rates of inbreeding, Genet. Sel. Evol. 32:231-248) or X'Mate™ (X'Prime) can be used if in-house software development is not feasible.

In certain embodiments of the invention, OGC can be implemented to limit or control inbreeding in a line development program utilizing Precision Breeding technology.

OGC software generally requires pedigree information and a description of the structure of a breeding program, including but not limited to, population size, test capacity and maximum parity of sows. With the use of Precision Breeding technology, one needs to also include the definition of age and genetic merit subclasses.

Instead of calculating the optimum genetic contribution for each of the performance tested individuals, when using Precision Breeding technology, one now calculates the optimum genetic contribution for each of the performance tested individuals for the production of male progeny and the optimum genetic contribution for each of the performance tested individuals for the production of female progeny. Individuals with a calculated contribution below a certain threshold for the production of males and below a certain threshold for the production of females are culled and the selected individuals are then available for breeding to produce male and/or female progeny. One produces a mating plan that minimizes inbreeding and results in the contributions that have been calculated.

Table 2 below gives an example of the calculated contributions of the selection candidates (male as well as female) to produce male and/or female progeny.

TABLE 2

| Genetic contributions: number of progeny | | | | Genetic contributions: number of progeny | | | | |
| --- | --- | --- | --- | --- | --- | --- | --- | --- |
| Selection Candidates | | Contribution to produce | | Selected | Selection Candidates | | Contribution to produce | | Selected |
| ID | Sex | males | females | Y/N | ID | Sex | males | females | Y/N |
| 1 | male | 32 | 72 | Yes | 7 | female | 8 | 32 | Yes |
| 2 | male | 0 | 48 | Yes | 8 | female | 0 | 0 | No |
| 3 | male | 0 | 16 | Yes | 9 | female | 0 | 16 | Yes |
| 4 | male | 64 | 56 | Yes | 10 | female | 16 | 40 | Yes |
| 5 | male | 0 | 0 | No | 11 | female | 24 | 40 | Yes |
| 6 | male | 0 | 0 | No | 12 | female | 0 | 0 | No |
| | | | | | 13 | female | 8 | 24 | Yes |
| | | | | | 14 | female | 40 | 40 | Yes |
| | | | | | 15 | female | 0 | 0 | No |
| | | | | | 16 | female | 0 | 0 | No |
| Total | | 96 | 192 | | Total | | 96 | 192 | |

The process may use iteration, most likely evolutionary algorithms, to find the optimum solution that meets all defined requirements. In this example requirements might have been:

A defined maximum level of increase of inbreeding

Maximize genetic improvement given the inbreeding restriction

Each contribution is a multiple of 8.

If one defines subgroups of animals, the target for each animal within one group will be the same.

The financial costs associated with the sex sorting process itself are a factor in its implementation in a production pyramid. These costs, however, can be mitigated by using low dose insemination techniques disclosed herein and/or by reducing the number of doses (inseminations) per estrus from two to one using the estrus synchronization techniques disclosed herein.

The process of producing sex sorted sperm cell samples is generally time consuming and expensive, typically requiring the use of specialized flow cytometry equipment, highly trained technicians and complex processes. Unfortunately, the typical dose of boar sperm cells required for successful fertilization using conventional artificial insemination techniques such as intra-cervical insemination is $1\times10^9$ sperm cells to $3\times10^9$ sperm cells, with the typical boar ejaculate containing approximately $6\times10^{10}$ sperm cells. Therefore, the typical boar ejaculate contains approximately 20 to 60 artificial insemination doses, greatly limiting the commercial application of sex sorted sperm cell samples in breeding swine. Furthermore, as noted above, females are generally inseminated two times per estrus cycle. Accordingly, if the total number of sperm cells needed for successful fertilization can be reduced, a greater number of artificial insemination doses can be produced for a given boar in a given amount of time, making the use of sex sorted sperm cell samples much more desirable from a commercial standpoint. In order to widen the commercial application of sex sorted sperm cell samples in swine, certain embodiments of the instant invention encompass methods of low dose insemination, including insemination via deep intra-uterine catheter and laparoscopy, and methods of synchronizing estrus. These methods make available the option of reducing the number of males produced for breeding in a production pyramid and consequently the number of sows used to produce these males used for breeding in a production pyramid. Alternatively, instead of reducing the production of males used for breeding, genetic dissemination through the production pyramid may be accelerated by selecting fewer, higher genetic merit males for breeding at each level of production, which ultimately results in higher quality commercial swine.

The following Examples are disclosed by way of example only, and are not intended to limit embodiments of the invention disclosed herein in any way.

Example 1

In the following Example, one is interested in the prediction of the average effect of using Precision Breeding technology in a swine breeding program using a deterministic method.

Step 1: Define a breeding program without the use of Precision Breeding technology (control):

Step 1.1: Define the sow herd for a line at the GN based on the following variables:
  Number of sows per parity
  Number of selected gilts entering the sow herd per period (e.g. week, year)
  Maximum parity for Sire lines and for Dam lines
  Age at production of first and subsequent litters Step 1.2: Define the population of boars
  Number of boars selected per period (e.g. week, year)
  Number of days boars are used for breeding.
  Age of boar at which first progeny are born Step 1.3: Production of progeny
  Available gilts and sows are randomly mated with available boars and each litter has a 50/50 split between male and female progeny.
  8 Piglets per litter (4 male and 4 female) available for performance test.
  Number of male and female progeny available for performance test per period.

Step 1.4: performance test
  Test eight progeny per litter.
  $NS^d$=number of gilts to select per period; $NPT^d$=number performance tested per period. The selected fraction for gilts ("$p^d$")=$NS^d/NPT^d$. Similarly, the selected fraction for boars ("$p^s$")=$NS^s/NPT^s$. The "d" stands for dam and the "s" stands for sire.
  p-values can be converted into selection intensities using a function of p, or looked up in tables.
  $L^d$ is the average age of the sows (dams) when progeny are born.
  $L^s$ is the average age of boars (sires) when the progeny are born.
  Genetic improvement $dG=R_{IH}*\sigma_H*(i^d+i^s)/(L^d+L^s)$. The "$\sigma_H$," genetic variation, is a constant and one assumes that the accuracy of selection $R_{IH}$ is the same for tested gilts and boars. So one can evaluate breeding program options by comparing the $(i^d+i^s)/(L^d+L^s)$ values.

Step 2: Define a breeding program with the use of Precision Breeding technology. The following details are important in addition to what has been described above:

Step 2.1: Define the sow herd:
  Split sows in subgroups based on genetic merit ("SowGGM").
  Number of sows per "Parity*SowGGM" subclass.

Step 2.2: Define the population of boars.
  Split the period boars are used for breeding into subgroups based on age and genetic merit ("BoarGGM").
  Average age of boars at which progeny are born for each Age*BoarGGM subgroup.

Step 2.3: Production of progeny
  For each (Parity*SowGGM)*(Age*BoarGGM) combination (i.e., for each mating subtype) allocate a certain percentage of male progeny to be produced with the remainder being female progeny. If for instance there are two parities and three SowGGM classes, two boar age classes and two BoarGGM classes, the percentage of male progeny needs to be allocated to 24 mating classes (i.e., 2*3*2*2=24).
  Number of male and female progeny available for performance test per period
  % male progeny produced per parity.
  % male progeny per boar age group.

Step 2.4: performance test
  Selected gilts and boars are split into subgroups based on their genetic merit and the group of best individuals will have a higher selection intensity than the second best group etc. The 'i' value can be calculated for each SowGGM and for each BoarGGM class.
  In the breeding program without Precision Breeding (i.e., the control situation), the same sows produce the male and female progeny. In the breeding program that uses Precision Breeding, the male progeny can be produced with a different mix of sows than the female progeny. Furthermore, in the control situation, the same boars produce the male and female progeny. Using Precision Breeding, the male progeny can be produced with a different mix of boars than the female progeny. Furthermore, when using Precision Breeding, there are effectively two types of sows (DD=sows producing female progeny and DS=sows producing male progeny) and two types of boars (SD=boars producing female progeny and SS=boars producing male progeny). Thus, when using Precision Breeding, genetic improvement $dG=R_{IH}*\sigma_H*(i^{dd}+i^{ds}+i^{sd}+i^{ss})/(L^{dd}+L^{ds}+L^{sd}+L^{ss})$. The $\sigma H$ is a constant and one assumes that the accuracy of selection $R_{IH}$ is the same for all tested gilts and boars. Thus, one can evaluate breeding program options by comparing the $(i^{dd}+i^{ds}+i^{sd}+i^{ss})/(L^{dd}+L^{ds}+L^{sd}+L^{ss})$ values.

Step 3: Maximizing Genetic Progress of the Breeding Program using Precision Breeding Step 3.1: "Control i/t"=$(i^d+i^s)/(L^d+L^s)$.

Step 3.2: Define options for the percentage of male progeny in the litters in each of the mating subtypes. Each of the mating subtypes might have 0, 10, 20, 30, 40, 50, 60, 70, 80, 90 or 100% male piglets produced. With, for example, 24 mating subtypes, that would result in $(11)^{24}$ options to evaluate.

Step 3.3: "Precision Breeding i/t"=$(i^{dd}+i^{ds}+i^{sd}+i^{ss})/(L^{dd}+L^{ds}+L^{sd}+L^{ss})$ for each option.

Step 3.4: $dG_{ratio}$="Precision Breeding i/t" divided by "Control i/t".

Step 3.5: The option with the highest value for $dG_{ratio}$ is close to the best.

Step 3.6: Define options for the percentage of male progeny in the litters in each of the mating classes around the best value found in step 3.5 with steps of 1% instead of 10%.

Step 3.7: Repeat steps 3.3 to 3.5 and search for the best value.

Alternatively, Step 3 can be performed using evolutionary algorithms. The 'solution' starts with a defined solution. This could in our example be 50%/50% male/female progeny per litter in each of the 24 mating types. The program then defines small deviations (for instance 49/51 and 51/49 for each mating type) and finds the best solution. The program then defines small deviations around the last solution and finds the best new solution etc., until the solution stabilizes.

Step 4: Repeat the process with different assumptions and for different strategies
  For Sire lines or Dam lines.
  Number of gilts entering the herd per cycle=50, 100, 150, 200, 300 etc.
  Number of boars used for breeding per cycle=10, 20, 30, 50, 100 etc.
  Maximum parity=1, 2, 3, 4, 5 or 6.
  Period boars are used for breeding=35 days, 70 days, 140 days etc.
  Split gilts/sows into 2, 3, 4, . . . genetic merit classes (or don't split).

Split breeding boars into 2, 3, 4, . . . genetic merit classes (or don't split).

Etc.

Example 2

Tables 3 to 5 below provide an example of a mating plan in a line development program that uses Precision Breeding technology. This mating plan comprises 30 females split into three parity subgroups and 4 males split into two male age subgroups, with each of those male and female subgroups further split into two genetic merit subgroups. A 100% farrowing rate was assumed. Table 3 gives the number of sows in each of the 24 mating subtype classes.

TABLE 3

| Number of litters per mating subtype[a] | | Age females[b] | | | | | Total nr of litters |
|---|---|---|---|---|---|---|---|
| Age males[c] | EBV[d] | P1 | | P2 | | P3 | |
| | | 1 | 2 | 1 | 2 | 1 | 2 | |
| 1 | 1 | 2 | 1 | 2 | 1 | 1 | 1 | 8 |
| 1 | 2 | 2 | 1 | 1 | 2 | 1 | 1 | 8 |
| 2 | 1 | 1 | 2 | 1 | 1 | 1 | 1 | 7 |
| 2 | 2 | 1 | 2 | 1 | 1 | 1 | 1 | 7 |
| Nr of females | | 6 | 6 | 5 | 5 | 4 | 4 | 30 |

[a]The table gives the number of litters produced per mating subtype (=combination of male subgroup and female subgroup).
[b]Females are split into three subgroups based on age (parity 1, 2 and 3).
[c]Males are split into two subgroups based on age (1 and 2).
[d]Females are split within parity into two EBV subgroups (1 and 2) and males are split within age group into two EBV subgroups (1 and 2).

Females are split within parity into two EBV subgroups (1 and 2) and males are split within age group into two EBV subgroups (1 and 2).

For each of the 24 mating subtypes, a target for the percentage of male progeny for each mating subtype is determined that, relative to a control, maximizes genetic progress in the line and keeps the increase of inbreeding at a defined level. Table 4 gives the target percentage of male progeny in each of the mating subtype classes.

TABLE 4

| % Male progeny per mating subtype[a] | | Age females[b] | | | | | |
|---|---|---|---|---|---|---|---|
| Age males[c] | EBV[d] | P1 | | P2 | | P3 | |
| | | 1 | 2 | 1 | 2 | 1 | 2 |
| 1 | 1 | 100 | 100 | 25 | 0 | 0 | 0 |
| 1 | 2 | 100 | 100 | 25 | 0 | 0 | 0 |
| 2 | 1 | 100 | 25 | 0 | 0 | 0 | 0 |
| 2 | 2 | 25 | 0 | 0 | 0 | 0 | 0 |

[a]The table gives the average percentage of males produced in litters per mating subtype (=combination of male subgroup and female subgroup).
[b]Females are split into three subgroups based on age (parity 1, 2 and 3).
[c]Males are split into two subgroups based on age (1 and 2).
[d]Females are split within parity into two EBV subgroups (1 and 2) and males are split within age group into two EBV subgroups (1 and 2).

The data from Tables 3 and 4 can then be used to determine the number of male piglets produced and available for performance testing, as shown in Table 5. Under this mating plan, it is assumed that 8 piglets per litter are available for performance testing.

TABLE 5

| Nr of male progeny per mating subtype[a] | | Age females[b] | | | | | Nr of male progeny |
|---|---|---|---|---|---|---|---|
| Age males[c] | EBV[d] | P1 | | P2 | | P3 | |
| | | 1 | 2 | 1 | 2 | 1 | 2 | |
| 1 | 1 | 16 | 8 | 4 | 0 | 0 | 0 | 28 |
| 1 | 2 | 16 | 8 | 2 | 0 | 0 | 0 | 26 |
| 2 | 1 | 8 | 4 | 0 | 0 | 0 | 0 | 12 |
| 2 | 2 | 2 | 0 | 0 | 0 | 0 | 0 | 2 |
| Nr of male progeny | | 42 | 20 | 6 | 0 | 0 | 0 | 68 |

[a]The table gives the number of males produced per mating subtype (=combination of male subgroup and female subgroup).
[b]Females are split into three subgroups based on age (parity 1, 2 and 3).
[c]Males are split into two subgroups based on age (1 and 2).
[d]Females are split within parity into two EBV subgroups (1 and 2) and males are split within age group into two EBV subgroups (1 and 2).

In this mating plan example, of all 240 progeny available for performance testing, 68 (28%) are male.

Example 3

The following Example demonstrates that by increasing the number of criteria to split males or females into subgroups (e.g. EBV, age, parity etc.), by increasing the number of subgroups for a given criterion, or by defining both male and female subgroups, one may increase the genetic progress of a line.

Programs using precision breeding (PB) were compared with a control program using a deterministic approach as described in Example 1.

Program parameters for sire line
- 150 first parity sows per cycle
- 10 boars selected per cycle of 5 months
- Boars split into 2 age groups and 2 EBV classes resulting in 4 subgroups
- Sows split into 2 age groups (parity 1 and 2) and 3 EBV classes resulting in 6 subgroups
- 24 mating subtypes (4*6)

Program parameters for dam line
- 200 first parity sows per cycle
- 15 boars selected per cycle of 5 months
- Boars split into 2 age groups and 2 EBV classes resulting in 4 subgroups
- Sows split into 3 age groups (parity 1, 2 and 3-5) and 3 EBV classes resulting in 9 subgroups
- 36 mating subtypes (4*9).

For the mating plan for the line that uses Precision Breeding technology, males were classified into two age groups: "younger males" (the first three months they are used) and "older males" (the subsequent three month period). The males were further classified by their EBVs into two groups ("HH" and "H"), with the first group comprising the very best boars ("HH") and second group comprising the second best boars ("H"). The females of a sire line were classified into two age groups: "1" (parity 1) and "2" (parity 2) while the females of a dam line were classified into three age groups: "1" (parity 1), "2" (parity 2) and "3" (parity 3-5). The gilts/sows were further classified into three groups of equal size based on their EBVs ("HH," "H" and "M," from highest to lowest breeding value).

Control: 50% male progeny in each mating subtype
PB-1: Same optimal percentage of male progeny in each mating subtype
PB-2: Optimal percentage of males in the first litter and 100% females in subsequent litters.

PB-3s: Sire line. The youngest boars are used on gilts to produce first litters with optimal percentage males. The oldest boars are used on sows to produce second litters with 100% females.

PB-3d: Dam line: The youngest boars are used on gilts to produce first litters with optimal percentage males and on sows to produce the second litters with 100% females. The oldest boars are used on sows to produce parity 2-5 litters with 100% females.

PB-4s: Sire line: Same as PB-3s but now making use of the EBV classes. The percentage of male progeny is optimized in each of the 6 EBV classes (2 boar EBV and 3 gilt EBV classes).

PB-4d: Dam line: Same as PB-3d but now making use of the EBV classes.

PB-5: Increase the number of EBV classes

PB-6: Each individual is treated as an EBV class.

Figure 2:
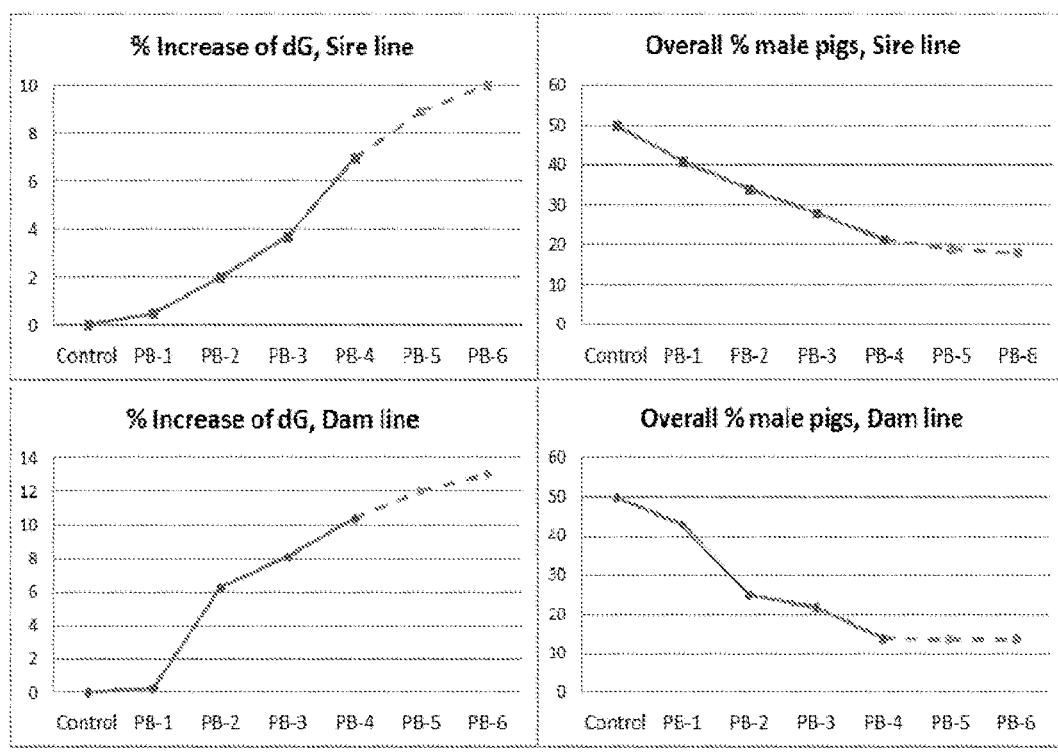
FIG. 2 shows the increase in dG and reduction in overall percentage of male progeny that results when Precision Breeding is applied with increased levels of sophistication in both sire and dam lines.

Evaluation was carried out for the programs PB-1 to PB-4. The last two programs, PB-5 and PB-6, have been estimated by extrapolating results. Results are summarized in FIG. 2, which shows that increased levels of sophistication in Precision Breeding lead to a larger impact on dG, up to about +10% in sire lines and +13% in dam lines. The overall percentage of male pigs drops to about 20% in sire lines and 15% in dam lines.

Example 4—Preparation of Sex Sorted Boar Sperm Cell Samples

The following process for the preparation of a sex sorted boar sperm cell sample is provided by non-limiting example only. The first step in the manufacture of sex sorted boar sperm cell sample is to obtain an ejaculate from a suitable boar. Once the ejaculate has been collected, it can be extended in a suitable extender, that may include an antioxidant. A sperm rich fraction of the ejaculate can then be diluted. If the sample needs to be transported prior to sex-selection, the sample can be held at a temperature of 0-39° C. (typically 16-17° C.) for between about 12 hours to about 18 hours while it is being shipped from the collection point to the flow cytometer for the sex-sorting process.

Once the sperm cell sample is in the laboratory, various quality checks can be conducted on the sperm cell sample including checking the motility (e.g., via CASA System), viability (e.g., via flow cytometry), morphology (e.g., via microscopy) and concentration (e.g., via NucleoCounter). Sperm cell samples that pass these quality checks are then prepared for sorting.

Prior to putting the sample through the flow cytometer, the sample is stained with a DNA selective dye, exposed to a quenching dye to form a stained sperm cell sample, which is subsequently placed into a sperm cell source of the flow cytometer. Specifically, the sperm cell sample in some embodiments, can be first diluted with a buffer or extender, such as BTS (see Table 6) to a final concentration which in some cases can be $100 \times 10^6$ cells/ml, and the DNA selective dye Hoechst 33342 (can be 5 mg/ml in MiliQ water; Ref: B-2261) is then added, a good working concentration can be about 5 µl/100 million cells/ml but DNA dye can be used at lower and higher concentrations in the range of 0.5 to 20 µl/100 million cells/ml. The sample is then usually placed in covered bath water between 30 and 42° C. (usually close to 35° C.) for between 10 min and 12 hours, with exceptional staining at about 50 minutes, and then subsequently placed in a dark area at room temperature (21-22° C.) prior to sorting. Before sorting the sample, the sample is filtered to remove large debris and cells (for example with CellTricks of 0.30 µm) and after filtering, red food dye may be added (when added, usually 0.5-5 µl, or 1 µl of a 25 mg/ml stock solution in MiliQ water) or another quenching dye, can be added to the sample. The sample can then be sorted using a flow cytometer with a sheath fluid which in some cases may comprise the components as listed in Table 7, but other sheath fluids may be used as well.

Figure 3:
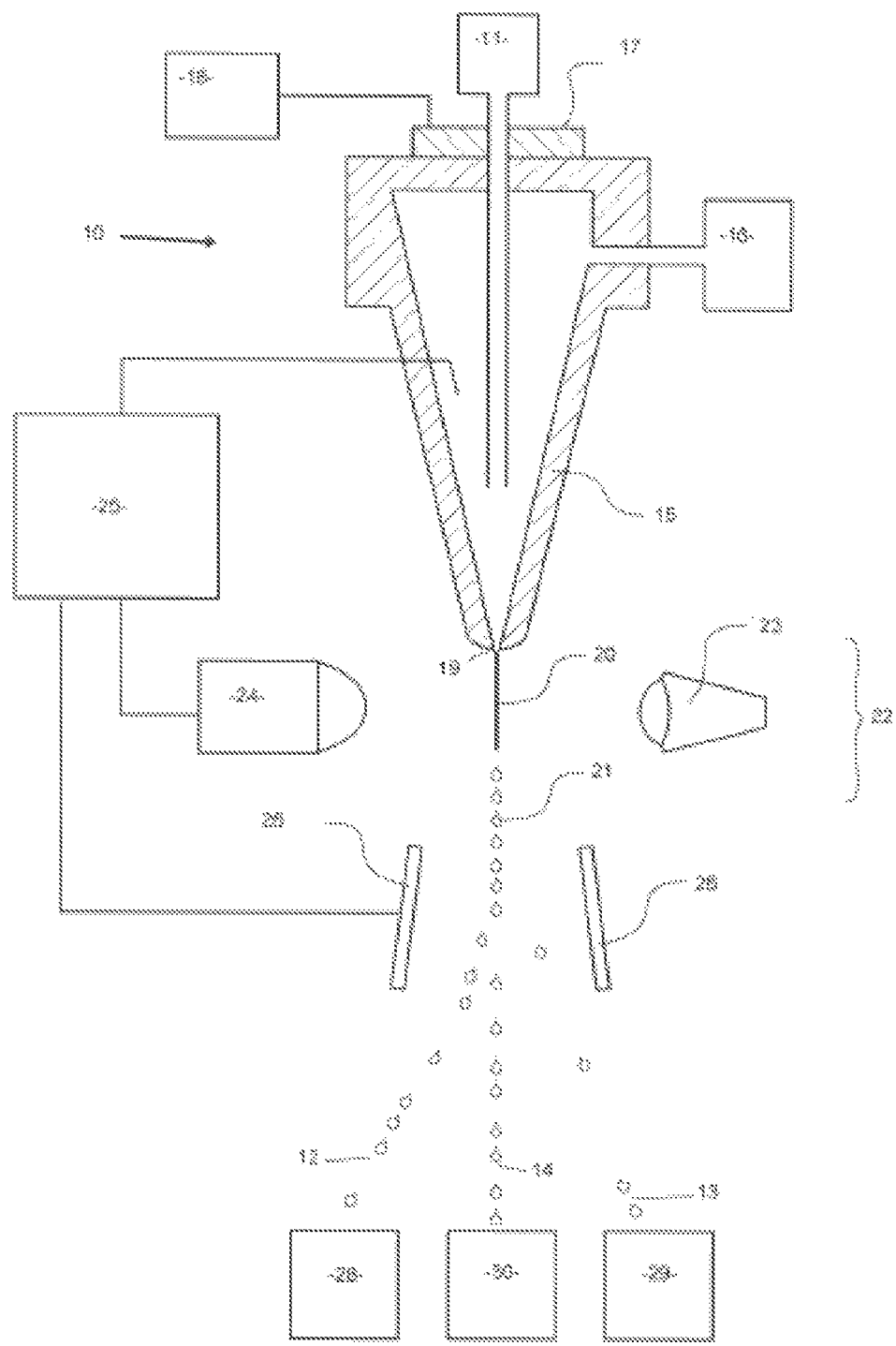
FIG. 3 illustrates schematically a flow cytometer that can be used to sort sperm cell samples into one or more subpopulations bearing X- or Y-chromosomes.

FIG. 3 illustrates, in schematic form, part of a flow cytometer used to sort a sperm cell sample to form one or more subpopulations, the flow cytometer being generally referenced as 10. In this particular embodiment, sex sorting is taking place so the subpopulations are X-chromosome bearing sperm cells and Y-chromosome bearing sperm cells. FIG. 3 represents a single technique for sorting sperm, but any known technique for sorting cells known in the art can be used with certain embodiments of the invention.

The flow cytometer 10 of FIG. 3 can be programmed by an operator to generate two charged droplet streams, one containing X-chromosome bearing sperm cells, charged positively, 12, one containing Y-chromosome bearing sperm cells, charged negatively 13 while an uncharged undeflected stream of dead cells 14 simply goes to waste.

An operator may also choose to program the flow cytometer in such a manner, that both the X- and Y-chromosome bearing sperm are collected using a "high purity sort" (in other words only live X- and Y-chromosome bearing sperm are collected) or to program the flow cytometer to collect both the X- and Y-chromosome bearing sperm using an "enriched sort" (in other words it will collect droplets containing live cells that were not previously sorted and excluding all initial dead cells again by the use of Boolean Gate logic available with the computer that controls the flow cytometer). The Boolean Gate logic can also be used to collect only one of either the X- or Y-chromosome bearing sperm.

Initially, a stream of sperm cells under pressure, is deposited into the nozzle 15 from the sperm cell source 11 in a manner such that they are able to be coaxially surrounded by a sheath fluid supplied to the nozzle 15 under pressure from a sheath fluid source 16. An oscillator 17 which may be present can be very precisely controlled via an oscillator control mechanism 18, creating pressure waves within the nozzle 15 which are transmitted to the coaxially surrounded sperm cell stream as it leaves the nozzle orifice 19. As a result, the exiting coaxially surrounded sperm cell stream 20 could eventually and regularly form droplets 21.

The charging of the respective droplet streams is made possible by the cell sensing system 22 which includes a laser 23 which illuminates the nozzle exiting stream 20, and the light emission of the fluorescing stream is detected by a sensor 24. The information received by the sensor 24 is fed to a sorter discrimination system 25 which very rapidly makes the decision as to whether to charge a forming droplet and if so which charge to provide the forming drop and then charges the droplet 21 accordingly.

A characteristic of X-chromosome bearing sperm is that they absorb more fluorochrome dye than Y-chromosome bearing sperm because of the presence of more DNA, and as such, the amount of light emitted by the laser excited absorbed dye in the X-chromosome bearing sperm differs from that of the Y-chromosome bearing sperm and this difference communicates to the sorter discrimination system 25 the type of charge to apply to the individual droplets which theoretically contain only a single X- or Y-chromosome bearing sperm cell. Dead cells (or those about to die) typically absorb the quenching dye which is communicated to the sorter discrimination system 25 not to apply a charge to the droplets containing such cells.

The charged or uncharged droplet streams then pass between a pair of electrostatically charged plates 26, which cause them to be deflected either one way or the other or not at all depending on their charge into respective collection vessels 28 and 29 to form respectively a gender enriched population of X-chromosome bearing and a gender enriched Y-chromosome bearing sperm cells having a DNA selective dye associated with their DNA. The uncharged non-deflected sub-population stream containing dead cells (or those about to die) go to the waste container 30.

The sex sorted sperm cell sample is collected in a 50 ml tube with 2.5 ml of catch fluid, which in some embodiments can be TesTrisGlucose (TTG) (see Table 8) with 2% of egg yolk, for every 20 million cells. In this embodiment, the sex sorted sperm cell sample will typically have a final volume of approximately 24 ml at about $1 \times 10^6$ cells per ml. This tube is then stored at room temperature in a dark room for about 2 hours.

TABLE 6

BTS Extender

| CHEMICALS | SYGMA CODE | g/liter |
|---|---|---|
| Glucose | G6152 | 36.941 |
| Sodium Citrate | S4641 | 5.999 |
| Sodium Bicarbonate | S5761 | 1.261 |
| EDTA | ED2SS | 1.250 |
| Potassium Chloride | P3911 | 0.7456 |
| Kanamycin sulfate | K4000 | 0.05 |

TABLE 7

Sheath Fluid (PBS)

| CHEMICALS | SYGMA CODE | g/liter |
|---|---|---|
| Sodium Chloride | S9888 | 8 |
| Potassium Chloride | P3911 | 0.2 |
| Sodiumphosphatemonobasicmonohydrate | S9638 | 0.12 |
| Sodiumphosphatedibasicheptahydrate | S9390 | 1.717 |
| EDTA acid | E6758 | 1 |
| Penicillin G potassium salt | PENK | 0.058 |
| Streptomycin Sulfate | S6501 | 0.05 |

TABLE 8

TesTrisGlucose (TTG)

| CHEMICALS | SYGMA CODE | g/100 ml |
|---|---|---|
| TES | T1375 | 5 |
| TRIS | T1503 | 0.68 |
| GLUCOSE | G6152 | 0.6 |
| KANAMICYN | K4000 | 0.005 |

Once the sex sorted sperm cell sample has been obtained, it can be used with conventional artificial insemination procedures, such as intra-cervical insemination, in vitro fertilization or artificial insemination with deep intrauterine catheter or laparoscopy. Alternatively, the sex sorted sperm cell sample can be cryopreserved for storage and then subsequently thawed out for use at a later time.

Example 5—Cryopreservation of Sex Sorted Boar Sperm Cell Samples

Once the sex sorted boar sperm cell sample has been manufactured, the sperm cell sample can be optionally cryopreserved for transport or storage for use at a later time. The following method of freezing can be used with the invention, but is presented by way of example only—any cryopreservation method known in the art can be used.

After sorting, the 50 ml tubes containing the sex sorted sperm cells (with 20 million cells) can be divided into tubes of 15 ml, with approximately 12 ml of a sex-select sperm cell sample semen in each tube, each containing approximately 10 million sex sorted sperm cells. Theses tubes can be centrifuged at 3076 g at 21° C. for 4 minutes. The supernatant decanted, and the pellet can remain with some of the supernatant in approximately 50 µl.

To each pellet, a first freezing medium, that may comprise a solution of 20% egg-yolk and 80% β-Lactose, can then be added at room temperature. The motility of the sperm cells can then be checked. If acceptable, the tubes can be taken to a programmable temperature control machine (PolyScience—MiniTube) or can be manually handled to decrease the temperature from about 21° C. to about 5° C. over a period of about 2 hours. After the timed temperature shift, the samples can be placed in a cold room at about 5° C. where a second freezing medium, which may comprise egg-yolk, β-Lactose, Glycerol and Equex Stem, or may just comprise a cryopreservative such as glycerol, or the cryopreservative with an osmotic stabilizer which is previously cooled to 5° C. is added to the samples. After 10 minutes, the sex sorted sperm cell samples can be placed in artificial insemination straws, and the straws then exposed to liquid nitrogen vapors (approximately 4 cm from the liquid nitrogen) for a short period of time (e.g. 10 minutes) and then placed directly into the liquid nitrogen for long term preservation.

When the sex sorted semen samples are ready for use, the straws can be unfrozen by thawing/warming the straws (e.g. place in a water bath set at about 37° C. for about 15 seconds). Post-thaw, motility and viability of the sperm cells can then be analyzed at 30, 90 and/or 150 minutes for standard comparisons.

Example 6—Estrus Synchronization

The invention contemplates that for convenience purposes, estrus can be synchronized and/or timed ovulation induced in one or more sows to be inseminated. Furthermore, because sex sorted sperm is often pre-capacitated, it is important to inseminate a sow within approximately 6 hours of ovulation. Synchronized estrus or timed ovulation helps assure this will be the case. Generally speaking this entails administering one or more hormone or hormone analogs to the sow(s) to be inseminated. There are several ways to induce estrus/timed ovulation in gilts, which are described below.

The one or more hormone or hormone analogs can be administered to the sow in order to establish estrus synchronization as well as time of ovulation. These hormones and hormone analogs typically include, for example, PG600, OvuGel, eCG, hCG, and/or progestin, and can be administered manually with timed injections or with the assistance of a programmable device placed in the reproductive tract of the sow. The programmable device contemplated herein releases one or more hormone or hormone analogs in a time released fashion without the breeder having to monitor the device or provide any input other than programming the initial parameters for release of said one or more hormone or hormone analogs. Any of the following methods for inducing and/or synchronizing estrus known in the art may be used generally with the invention, including the following.

(a) Transport and Boar Induced Estrus.

Gilts typically attain puberty at approximately 180-210 days of age. However, the natural attainment of puberty is influenced by many intrinsic and extrinsic factors, such as genotype, environment and boar contact. Many breeders and farmers indicate that the first estrus is commonly observed when gilts are six months of age. The onset of estrus often coincides with relocation or transport of animals from the gilt multiplier to the commercial farm. Undoubtedly, the best-known stress factor in pigs is that of transportation. If the age of gilts at the time of transport is close to the normal onset of puberty, approximately 25-35% of gilts will display estrus within one week after transport. This transport-induced estrus can serve to synchronize a proportion of gilts.

Although transport may induce estrus, it is evident that boar contact is a potent form of puberty stimulation. The major factor controlling the efficiency of boar contact as a puberty stimulus is the age of the gilt at the time of boar introduction. When boar contact is initiated when gilts are 4 months of age, the pubertal response is minimal. It was suggested that the young gilt may become habituated to the boar stimulus at a stage in development when she is too young to respond. Conversely, when boar introduction is delayed until the immediate prepubertal period (6 months of age and above), the response is again limited for a different reason. By virtue of the relatively old ages, i.e. 6 months, of gilts at introduction, the actual pubertal ages of these gilts are not much reduced below those of unstimulated animals. When boar introduction occurs at gilt ages in the region of 160 days, both the interval from first boar contact to puberty and gilt age at puberty are minimized, while maximum synchronization of the pubertal estrus occurs.

(b) Oral and Time-Release Progestins.

This approach to estrus synchronization utilizes suppression of ovarian activity through the administration of orally administered progesterone or synthetic progestins. Some progestins can be obtained that are timed-release injectible forms, such as altrenogest (see below). Feeding cyclic gilts individually or in groups at a rate of 15-30 mg altrenogest/pig/day for 14 to 18 consecutive days produces a synchronous onset of estrus between 2 and 8 days after the last progestin feeding.

(c) Gonadotropins.

eCG/hCG (PG600R) Presently, the most common exogenous hormone combination for induction of follicle growth and ovulation in acyclic females is a combination of eCG, formerly called pregnant mare's serum gonadotropin (PMSG), and human chorionic gonadotropin (hCG). The product PG600R contains 400 IU PMSG and 200 IU hCG. This hormone can be purchased as a combination drug and is cost-effective for the induction of estrus and ovulation in acyclic pigs. Gilts usually show estrus 3-6 days after treatment and the time of ovulation is approximately 110-120 hours. The response rate is enhanced if gilts are given daily boar contact, beginning at the time of treatment. PG600 comprises pregnant mare's serum gonadotropin, otherwise known as equine chorionic gonadotropin ("PMSG" or "eCG") and human chorionic gonadotropin ("hCG") (Intervet). OvuGel is another commercially available gonadotropin (triptorelin acetate) in a slow release formula which can be administered via an intravaginal delivery system (Gel Med Sciences, Inc.).

(d) Prostaglandins.

PGF2 alpha is effective for inducing luteolysis, abortion, and a prompt return to estrus in pregnant (and pseudopregnant) gilts beyond the second week of pregnancy. One method for synchronization is to pen-mate gilts for three weeks and then, treat with PGF2 alpha two weeks later.

(e) Time-Release Hormones.

Another method involves the direct injection of a commercially available preparation, such as altrenogest or regumate, at a specific time point in the estrus cycle. For example, in one embodiment of the invention, synchronization and timed ovulation is achieved by administering on day 11-14 of a gilt's estrus cycle, 15-30 mg altrenogest/day for 4 to 7 days. 24 hours after stopping altrenogest, 400 to 2000 IU of PMSG can be administered, and then 500 to 1000 IU of hCG, 72 to 83 hours later.

Example 7—Ovulation Detection

Ovulation detection in a sow can be done by examining the sow's follicles. The realization of the importance of establishing an adequate sperm reservoir in the oviduct at an appropriate time relative to ovulation is critical in the management of artificial insemination in swine. In particular, knowledge of when a sow is likely to ovulate during estrus is highly beneficial to achieving successful insemination. To that end, in a particular embodiment of the invention, sow's follicles are examined using ultrasound after the induction of estrus. In a specific embodiment of the invention, the sow's ovaries are examined by transrectal ultrasound every 4 hours beginning 30 hours after hCG injection for the presence of pre-ovulatory follicles. Sows showing multiple pre-ovulatory follicles (diameter of antrum>6 mm) are selected for insemination 2-3 hours after ultrasound.

Example 8—Insemination Using Laparoscopy or Deep Intrauterine Catheter

Once the sex sorted boar semen sample has been prepared, the sample can be used to inseminate a sow. Any conventional artificial insemination technique can be used in the invention, including intra-cervical insemination. However, deep intrauterine catheters and laparoscopy are particularly relevant in swine, since they allow for the use of a reduced dose of sperm cells for successful fertilization, in part because they are able to place the sperm cells in key areas of the sow's reproductive tract, including but not limited to the uterine horns, the oviducts, the ampulla, the isthmus and the utero-tubal junction. The use of reduced sperm cell doses allows the use of far fewer genetically superior boars for breeding purposes, which has the benefits of reducing costs to breeders and reducing the environmental harm that results from having to maintain a large number of boars.

(a) Insemination Using Deep Intrauterine Catheter. The use of a deep intrauterine catheter allows one to place sperm cells into the uterine horns of the sow and ideally at the utero-tubal junction. The use and construction of such a deep intrauterine catheter is disclosed in U.S. Pat. No. 6,695,767, the disclosure of which is hereby incorporated by reference in its entirety. Such a deep intrauterine catheter can optionally comprise a video camera or scope to allow the operator to see the path of the catheter, so that a choice between placing sperm cells in one or both of the uterine horns can be made. Alternatively, the location of the deep intrauterine catheter can be visualized within a reproductive tract of a sow when used in conjunction with a radiographic or fluoroscopic device. Because of its length, a deep intrauterine catheter allows the operator to reach distal regions of a sow's reproductive tract, including the uterine horns—regions that would be unreachable using a standard catheter used for artificial insemination. In one embodiment of the invention, the length of the deep intrauterine catheter is 1.8 m, 1-2 m, 1-2.5 m, 1-3 m, 2-3 m, 2-3.5 m or 2.5-3 m.

The deep intrauterine catheter can be introduced inside of the cervical duct of a sow in estrus which may be superovulated but may also be naturally cycling or otherwise induced. A non-toxic lubricant liquid can be applied onto the catheter to facilitate its passage through the vagina. The catheter can comprise an outer tube or sheath and a flexible probe within the outer tube or sheath. In one embodiment of the invention, once the catheter has been advanced to the cervical duct, the flexible probe can be further advanced within the outer tube of the catheter. The flexible probe can be advanced until reaching the anterior portion of a uterine horn. When the flexible probe is advanced within the uterine horn, it can bend and thus continue to follow the tortuous path of the uterine horn. Although it is not absolutely necessary, introduction of small volumes of liquid through the outer tube of the catheter can facilitate progression of the flexible probe at its passage through the cervical duct and its progression through the uterine horn. Once the flexible probe has been introduced up to its final position within the uterine horn, a sperm cell sample contained in a syringe being connected to the proximal end of the flexible probe and can be introduced—through a flexible duct within the flexible probe—into the uterine environment. So as to avoid losses of sperm cells and to ensure that the sperm cell sample has been completely evacuated from the flexible duct, a small volume of liquid can be subsequently introduced through the flexible duct. Thereafter, the catheter, comprising the outer tube and the flexible probe, can be withdrawn. In another aspect of the invention, this process can also be used for transferring embryos into a uterine horn or removing embryos from a uterine horn.

(b) Insemination Using Laparoscopy. Use of laparoscopy to inseminate a sow has the advantage that the placement of sperm cells within the sow's reproductive tract can be even more precise than with the use of a catheter, thus further enabling the use of reduced sperm cell doses for insemination. Specific areas of the uterus can be targeted, such as the oviduct, the isthmus, ampulla, or the utero-tubal junction. By way of a non-limiting example, the following procedure can be used with the invention to inseminate a sow via laparoscopy.

For example, a 50 ml tube containing 24 ml of a sex sorted sperm cell sample having about $1 \times 10^6$ sperm cells per ml can be divided into 2 tubes of 15 ml and centrifuged at about 3076 g at a temperature in the range of about 21° C. for several minutes (2-5 or 4 minutes). The supernatant can be recentrifuged under the same conditions if needed. The resulting semen pellets are then mixed and the concentration checked (via NucleoCounter). The concentrated sex sorted sperm cell sample is then diluted with BTS to a final concentration of $10 \times 10^6$ cells/ml and the motility and viability of the sperm cells is checked. (The sperm cell sample should be maintained at room temperature (21° C.) during the entire process.)

Sows can be grouped or separated, for instance they can be allocated individually to stalls in a mechanically ventilated confinement facility. Sows (2-6 parity) are weaned at about 21 days. Estrus can then be induced by injecting each female intramuscularly with about 1250 IU equine chorionic gonadotrophin (eCG; Folligon, Intervet International B.V., Boxmeer, The Netherlands—or an equivalent compound) 24 hours after weaning; 72 hours later, they are treated with about 750 IU human chorionic gonadotrophin (hCG; Veter-inCorion, Divasa, Farmavic S.A., Barcelona, Spain) or an equivalent. Estrus detection is performed once a day (for instance at 7:00 a.m.), beginning 2 days after eCG injection. One way to detect estrus is to allow females nose to nose contact with a mature boar and by applying back pressure, to identify sows that exhibit a standing heat reflex, which are considered to be in estrus; at which point the ovaries can be scanned. The ovaries can be examined at periodic intervals (e.g. every 4 hours) for mature follicles starting at about 30 hours after hCG injection by transrectal ultrasonography using a 5 MHz multiple scan angle transducer, to look for the presence of pre-ovulatory follicles. Only sows showing multiple pre-ovulatory follicles (diameter of antrum>6 mm) are selected for insemination. Inseminations are carried out within 2-3 h after ultrasonography.

Laparoscopic inseminations can then be performed on these sows once sedated (which may be by azaperone administration; Stresnil; 2 mg/kg body weight, i.m.). General anesthesia can also be induced with a compound such as sodium thiopental (Abbot; 7 mg/kg body weight, i.v.) and maintained with halothane (3.5-5%) or a similar compound. For surgery, the sow can be placed in the supine position, and if available, on her back in a laparoscopy cradle. If a cradle is used, it is placed in a Trendelenburg position (hind quarters upward, with the head pointing down) at an angle of approximately 20° above horizontal.

In one embodiment, an incision (about 1.5 cm) is made close to the umbilicus. The edges of the incision can then be pulled up with countertraction and a 12 mm Optiview trocar (Ethicon Endo-surgery Cincinnati Ohio, USA) with an inserted 0° laparoscope is advanced into the wound. At the umbilicus, the subcutaneous fatty tissue, the anterior fascia of the rectus muscles, the rectus muscles, the posterior fascia of the rectus muscles, the transversalis fascia and the peritoneum are traversed by slight cutting and moderate pressure. The process is controlled via monitor feedback. Although the $CO_2$ tubing is connected to the trocar, inflation does not begin until the peritoneum is punctured. After the peritoneal cavity is entered and the pneumoperitoneum started, the handpiece of the Optiview is removed and replaced by the 0° laparoscope. The abdominal cavity is inflated to 14 mmHg with $CO_2$. Two accessory ports are placed in the right and left part of the hemi abdomen, which provides access for laparoscopic Duval forceps for manipulating the uterine horn and grasping the oviduct for the insemination needle, respectively. The oviduct is grasped with the Duval forceps in the isthmus region. Then the dose-flow (containing 0.3-0.5 million of spermatozoa in 0.1 ml) is inserted, and sex sorted spermatozoa are flushed into the oviduct. The procedure is then repeated on the other oviduct. After both oviducts are inseminated, the trocars are removed and incision wounds sutured.

Those of ordinary skill in the art will recognize that the invention described above includes many inventive embodiments, including at least the following:
A. A method of increasing genetic merit of swine comprising the steps of:
establishing a plurality of mating subtypes for a line;
determining a percentage of progeny that are male for each of the mating subtypes, or a percentage of progeny that are female for each of the mating subtypes, that would result, relative to a control, in an increase in genetic merit in the line;
sorting a sperm cell sample from a male swine in one of the mating subtypes into one or more subpopulations of sperm cells, wherein at least 60% of sperm cells in a subpopulation of sperm cells bear X chromosomes or Y chromosomes; and inseminating one or more female swine in the one of the mating subtypes with the subpopulation of sperm cells to achieve the percentage of progeny that are male or the percentage of progeny that are female determined to increase genetic merit relative to a control.

A1. The method of A, wherein the percentage of progeny that are male, or the percentage of progeny that are female, determined to increase genetic merit, does not increase inbreeding in the line relative to the control.

A2. The method of A or A1, wherein the line comprises a sire line or dam line.

A3. The method of any of A to A2, wherein in the control, approximately 50% of progeny are male.

A4. The method of any of A to A3, wherein in the control, all female swine to be mated are inseminated with unsorted semen samples.

A5. The method of any of A to A4, wherein a category of male swine in one or more of the mating subtypes is defined by one or more characteristics, including genetic merit or age.

A6. The method of any of A to A5, wherein a category of female swine in one or more of the mating subtypes is defined by one or more characteristics, including genetic merit or parity.

A7. The method of any of A to A6, wherein the percentage of sperm cells in the subpopulation of sperm cells that bear X chromosomes or Y chromosomes is selected from the group consisting of at least 65%, at least 70%, at least 75%, at least 80%, at least 85%, at least 90%, at least 95%, at least 96%, at least 97%, at least 98%, at least 99% and at least 100%.

A8. The method of any of A to A7, wherein the line comprises a sire line and the percentage of progeny that are male for each of the mating subtypes, or the percentage of progeny that are female for each of the mating subtypes, determined to increase genetic merit of the line relative to a control, results in a percentage of progeny that are male for the line that is between approximately 10 to 35%.

A9. The method of A8, wherein the percentage of progeny that are male for the line is between approximately 15 to 30%.

A10. The method of any of A to A7, wherein the line comprises a dam line and the percentage of progeny that are male for each of the mating subtypes, or the percentage of progeny that are female for each of the mating subtypes, determined to increase genetic merit of the line relative to a control, results in a percentage of progeny that are male for the line that is between approximately 5 to 30%.

A11. The method of A10, wherein the percentage of progeny that are male for the line is between approximately 10 to 25%.

A12. The method of any of A to A7, wherein the percentage of progeny that are male for each of the mating subtypes, or the percentage of progeny that are female for each of the mating subtypes is between approximately 0 to 10% or between approximately 90 to 100% and any produced progeny are members of a daughter nucleus or a multiplier.

A13. The method of any of A to A12, wherein each of the mating subtypes in the plurality of mating subtypes comprises only one male swine or only one female swine from the line.

A14. The method of any of A to A13, wherein each of the mating subtypes in the plurality of mating subtypes comprises only one male swine and only one female swine from the line.

A15. The method of any of A to A14, wherein the determined percentages are determined using a stochastic or a deterministic method.

A16. The method of any of A to A15, wherein genetic merit of a male or a female is a function of one or more dam line traits.

A17. The method of any of A to A15, wherein genetic merit of a male or a female is a function of one or more sire line traits.

A18. The method of any of A or A15, wherein genetic merit of a male or a female is a function of a selection index.

A19. The method of any of A or A15, wherein genetic merit of a male or a female is a function of EBV.

A20. The method of A18, wherein the selection index is a function of data derived from a group comprising the male or the female.

A21. The method of A16, wherein the traits comprise fertility, litter size and milk production.

A22. The method of A17, wherein the traits comprise feed efficiency, average daily gain and carcass lean.

A23. The method of any of A to A22, wherein inseminating the one or more female swine comprises administering the subpopulation to a reproductive tract of the one or more female swine using a deep intrauterine catheter or a needle inserted through a membrane of the one or more female swine.

A24. The method of A23, wherein administering the subpopulation to a reproductive tract of the one or more female swine using a deep intrauterine catheter comprises placing said sperm cells in one or more uterine horns.

A25. The method of A23 or A24, wherein said deep intrauterine catheter comprises a video camera or scope.

A26. The method of any of A23 to A25, further comprising the step of visualizing the deep intrauterine catheter via radiography or fluoroscopy while inserted in said sow's reproductive tract.

A27. The method of any of A to A26, wherein the subpopulation comprises $1\times10^9$ or less sperm cells.

A28. The method of A23, wherein administering the subpopulation to a reproductive tract of the one or more female swine using a needle inserted through a membrane of the one or more female swine comprises injecting the subpopulation into one or more oviducts of the one or more female swine.

A29. The method of A28, further comprising the step of visualizing said needle being inserted into said one or more oviducts via a laparoscope or video camera.

A30. The method of any of A to A23 and A28 to A29, wherein the subpopulation comprises $1\times10^6$ or less sperm cells.

A31. The method of any of A to A30 further comprising the step of synchronizing estrus or inducing timed ovulation in the one or more female swine by administering one or more hormone or hormone analogs to the one or more female swine.

A32. The method of A31, wherein the one or more hormone or hormone analogs comprises PG600, OvuGel, eCG, progestin, hCG, altrenogest or regumate.

A33. The method of A31 or A32, wherein the one or more hormone or hormone analog is administered by a programmable device placed in the reproductive tract of the one or more female swine.

A34. The method of any of A to A33, further comprising the step of detecting ovulation in the one or more female swine by examining one or more follicles of the one or more female swine.

A35. The method of A34, wherein the one or more follicles are examined using ultrasound.

A36. The method of any of A to A35, comprising the additional step of selecting parents based on phenotypic measurement.

A37. The method of any of A to A35, comprising the additional step of selecting parents for the line based on genotype.

A38. The method of any of A to A35, comprising the additional step of selecting parents using mutation assisted selection.

A39. The method of any of A to A35, wherein genetic merit is based on phenotypic measurement.

A40. The method of any of A to A35, wherein genetic merit is based on genotype.

A41. The method of any of A to A40, wherein the male swine or the one or more female swine are members of a genetic nucleus, a daughter nucleus or a multiplier.

A42. The method of any of A to A40, wherein the male swine or the one or more female swine are members of a genetic nucleus.

A43. The method of any of A to A42, wherein the step of establishing a plurality of mating subtypes for a line is performed as part of a breeding program.

A44. The method of any of A to A42, wherein the step of establishing a plurality of mating subtypes for a line is performed as part of creating a mating plan for the line.

A45. The method of any of A to A44, wherein each of the mating subtypes for the line is comprised of a male subgroup or a female subgroup.

A46. The method of A45, wherein the male subgroup or the female subgroup is defined or based on one more criteria comprising function in the production pyramid, parity, age, genetic merit, genetic markers, or genetic mutations.

B. A method of increasing genetic merit of swine comprising the steps of:
establishing a plurality of mating subtypes for a line; and determining a percentage of progeny that are male for each of the mating subtypes, or a percentage of progeny that are female for each of the mating subtypes, that would result, relative to a control, in an increase in genetic merit in the line.

B1. The method of B, wherein the percentage of progeny that are male, or the percentage of progeny that are female, determined to increase genetic merit, does not increase inbreeding in the line relative to the control.

B2. The method of B or B1, wherein the line comprises a sire line or dam line.

B3. The method of any of B to B2, wherein in the control, approximately 50% of progeny are male.

B4. The method of any of B to B3, wherein in the control, all female swine to be mated are inseminated with unsorted semen samples.

B5. The method of any of B to B4, wherein a category of male swine in one or more of the mating subtypes is defined by one or more characteristics, including genetic merit or age.

B6. The method of any of B to B5, wherein a category of female swine in one or more of the mating subtypes is defined by one or more characteristics, including genetic merit or parity.

B7. The method of any of B to B6, wherein at least 80% of sperm cells in the first subpopulation bear X chromosomes or wherein at least 80% of sperm cells in the first subpopulation bear Y chromosomes.

B8. The method of any of B to B7, wherein the line comprises a sire line and the percentage of progeny that are male for each of the mating subtypes, or the percentage of progeny that are female for each of the mating subtypes, determined to increase genetic merit of the line relative to a control, results in a percentage of progeny that are male for the line that is between approximately 10 to 35%.

B9. The method of B8, wherein the percentage of progeny that are male for the line is between approximately 15 to 30%.

B10. The method of any of B to B7, wherein the line comprises a dam line and the percentage of progeny that are male for each of the mating subtypes, or the percentage of progeny that are female for each of the mating subtypes, determined to increase genetic merit of the line relative to a control, results in a percentage of progeny that are male for the line that is between approximately 5 to 30%.

B11. The method of B10, wherein the percentage of progeny that are male for the line is between approximately 10 to 25%.

B12. The method of any of B to B7, wherein the percentage of progeny that are male for each of the mating subtypes, or the percentage of progeny that are female for each of the mating subtypes is between approximately 0 to 10% or between approximately 90 to 100% and the produced progeny are members of a daughter nucleus or a multiplier.

B13. The method of any of B to B12, wherein each of the mating subtypes in the plurality of mating subtypes comprises only one male swine or only one female swine from the line.

B14. The method of any of B to B13, wherein each of the mating subtypes in the plurality of mating subtypes comprises only one male swine and only one female swine from the line.

B15. The method of any of B to B14, wherein the determined percentages are determined using a stochastic or a deterministic method.

B16. The method of any of B to B15, wherein genetic merit of a male or a female is a function of one or more dam line traits.

B17. The method of any of B to B15, wherein genetic merit of a male or a female is a function of one or more sire line traits.

B18. The method of any of B or B15, wherein genetic merit of a male or a female is a function of a selection index.

B19. The method of any of B or B15, wherein genetic merit of a male or a female is a function of EBV.

B20. The method of B18, wherein the selection index is a function of data derived from a group comprising the male or the female.

B21. The method of B16, wherein the traits comprise fertility, litter size and milk production.

B22. The method of B17, wherein the traits comprise feed efficiency, average daily gain and carcass lean.

C. A method of increasing genetic merit in a sire line comprising the steps of:
sorting one or more sperm cell samples from one or more male swine in the sire line into one or more subpopulations of sperm cells, wherein at least 70% of sperm cells in a subpopulation bear X chromosomes or Y chromosomes; and inseminating one or more female swine in the sire line with the subpopulation to achieve a percentage of progeny that are male for the sire line that is between approximately 10 to 35%.

C1. The method of C, wherein the percentage of progeny that are male for the sire line is between approximately 15 to 30%.

C2. The method of C or C1, wherein inseminating the one or more female swine comprises administering the subpopulation to a reproductive tract of the one or more female swine using a deep intrauterine catheter or a needle inserted through a membrane of the one or more female swine.

C3. The method of C2, wherein administering the subpopulation to a reproductive tract of the one or more female swine using a deep intrauterine catheter comprises placing said sperm cells in one or more uterine horns.

C4. The method of C2 or C3, wherein said deep intrauterine catheter comprises a video camera or scope.

C5. The method of any of C2 to C4, further comprising the step of visualizing the deep intrauterine catheter via radiography or fluoroscopy while inserted in said sow's reproductive tract.

C6. The method of any of C to C5, wherein the subpopulation comprises $1\times10^9$ or less sperm cells.

C7. The method of C2 or C6, wherein administering the subpopulation to a reproductive tract of the one or more female swine using a needle inserted through a membrane of the one or more female swine comprises injecting the subpopulation into one or more oviducts of the one or more female swine.

C8. The method of C7, further comprising the step of visualizing said needle being inserted into said one or more oviducts via a laparoscope or video camera.

C9. The method of any of C to C8, wherein the subpopulation comprises $1\times10^6$ or less sperm cells.

C10. The method of any of C to C9 further comprising the step of synchronizing estrus or inducing timed ovulation in the one or more female swine by administering one or more hormone or hormone analogs to the one or more female swine.

C11. The method of C10, wherein the one or more hormone or hormone analogs comprises PG600, OvuGel, eCG, progestin, hCG, altrenogest or regumate.

C12. The method of C10 or C11, wherein the one or more hormone or hormone analog is administered by a programmable device placed in the reproductive tract of the one or more female swine.

C13. The method of any of C to C12, further comprising the step of detecting ovulation in the one or more female swine by examining one or more follicles of the one or more female swine.

C14. The method of C13, wherein the one or more follicles are examined using ultrasound.

D. A method of increasing genetic merit in a dam line comprising the steps of:
sorting one or more sperm cell samples from one or more male swine in the dam line into one or more subpopulations of sperm cells, wherein at least 70% of sperm cells in a subpopulation bear X chromosomes or Y chromosomes; and inseminating one or more female swine in the dam line with the subpopulation to achieve a percentage of progeny that are male for the dam line that is between approximately 5 to 30%.

D1. The method of D, wherein the percentage of progeny that are male for the dam line is between approximately 10 to 25%.

D2. The method of D or D1, wherein inseminating the one or more female swine comprises administering the subpopulation to a reproductive tract of the one or more female swine using a deep intrauterine catheter or a needle inserted through a membrane of the one or more female swine.

D3. The method of D2, wherein administering the subpopulation to a reproductive tract of the one or more female swine using a deep intrauterine catheter comprises placing said sperm cells in one or more uterine horns.

D4. The method of D2 or D3, wherein said deep intrauterine catheter comprises a video camera or scope.

D5. The method of any of D2 to D4, further comprising the step of visualizing the deep intrauterine catheter via radiography or fluoroscopy while inserted in said sow's reproductive tract.

D6. The method of any of D to D5, wherein the subpopulation comprises $1\times10^9$ or less sperm cells.

D7. The method of D2 or D6, wherein administering the subpopulation to a reproductive tract of the one or more female swine using a needle inserted through a membrane of the one or more female swine comprises injecting the subpopulation into one or more oviducts of the one or more female swine.

D8. The method of D7, further comprising the step of visualizing said needle being inserted into said one or more oviducts via a laparoscope or video camera.

D9. The method of any of D to D8, wherein the subpopulation comprises $1\times10^6$ or less sperm cells.

D10. The method of any of D to D9 further comprising the step of synchronizing estrus or inducing timed ovulation in the one or more female swine by administering one or more hormone or hormone analogs to the one or more female swine.

D11. The method of D10, wherein the one or more hormone or hormone analogs comprises PG600, OvuGel, eCG, progestin, hCG, altrenogest or regumate.

D12. The method of D10 or D11, wherein the one or more hormone or hormone analog is administered by a programmable device placed in the reproductive tract of the one or more female swine.

D13. The method of any of D to D12, further comprising the step of detecting ovulation in the one or more female swine by examining one or more follicles of the one or more female swine.

D14. The method of D13, wherein the one or more follicles are examined using ultrasound.

E. A method of increasing genetic merit of swine comprising creating a mating plan for a line of swine to increase the genetic merit in the line relative to a control by establishing a plurality of mating subtypes for the line and determining a percentage of progeny that are male for each of the mating subtypes, or a percentage of progeny that are female for each of the mating subtypes, that would result, relative to the control, in an increase in genetic merit in the line.

E1. The method of E, wherein the percentage of progeny that are male, or the percentage of progeny that are female, determined to increase genetic merit, does not increase inbreeding in the line relative to the control.

E2. The method of E or E1, wherein the line comprises a sire line or dam line.

E3. The method of any of E to E2, wherein in the control, approximately 50% of progeny are male.

E4. The method of any of E to E3, wherein in the control, all female swine to be mated are inseminated with unsorted semen samples.

E5. The method of any of E to E4, wherein a category of male swine in one or more of the mating subtypes is defined by one or more characteristics, including genetic merit or age.

E6. The method of any of E to E5, wherein a category of female swine in one or more of the mating subtypes is defined by one or more characteristics, including genetic merit or parity.

E7. The method of any of E to E6, wherein at least 80% of sperm cells in the first subpopulation bear X chromosomes or wherein at least 80% of sperm cells in the first subpopulation bear Y chromosomes.

E8. The method of any of E to E7, wherein the line comprises a sire line and the percentage of progeny that are male for each of the mating subtypes, or the percentage of progeny that are female for each of the mating subtypes, determined to increase genetic merit of the line relative to a control, results in a percentage of progeny that are male for the line that is between approximately 10 to 35%.

E9. The method of E8, wherein the percentage of progeny that are male for the line is between approximately 15 to 30%.

E10. The method of any of E to E7, wherein the line comprises a dam line and the percentage of progeny that are male for each of the mating subtypes, or the percentage of progeny that are female for each of the mating subtypes, determined to increase genetic merit of the line relative to a control, results in a percentage of progeny that are male for the line that is between approximately 5 to 30%.

E11. The method of E10, wherein the percentage of progeny that are male for the line is between approximately 10 to 25%.

E12. The method of any of E to E7, wherein the percentage of progeny that are male for each of the mating subtypes, or the percentage of progeny that are female for each of the mating subtypes is between approximately 0 to 10% or between approximately 90 to 100% and the produced progeny are members of a daughter nucleus or a multiplier.

E13. The method of any of E to E12, wherein each of the mating subtypes in the plurality of mating subtypes comprises only one male swine or only one female swine from the line.

E14. The method of any of E to E13, wherein each of the mating subtypes in the plurality of mating subtypes comprises only one male swine and only one female swine from the line.

E15. The method of any of E to E14, wherein the determined percentages are determined using a stochastic or a deterministic method.

E16. The method of any of E to E15, wherein genetic merit of a male or a female is a function of one or more dam line traits.

E17. The method of any of E to E15, wherein genetic merit of a male or a female is a function of one or more sire line traits.

E18. The method of any of E or E15, wherein genetic merit of a male or a female is a function of a selection index.

E19. The method of any of E or E15, wherein genetic merit of a male or a female is a function of EBV.

E20. The method of E18, wherein the selection index is a function of data derived from a group comprising the male or the female.

E21. The method of E16, wherein the traits comprise fertility, litter size and milk production.

E22. The method of E17, wherein the traits comprise feed efficiency, average daily gain and carcass lean.

E23. The method of any of E to E22, wherein the line belongs to a genetic nucleus, a daughter nucleus or a multiplier.

E24. The method of any of E to E22, wherein the line belongs to a genetic nucleus.

E25. The method of any of E to E24, wherein the step of establishing a plurality of mating subtypes for a line is performed as part of a breeding program.

E26. The method of any of E to E24, wherein the step of establishing a plurality of mating subtypes for a line is performed as part of creating a mating plan for the line.

F. A method of increasing genetic merit of swine comprising the steps of:
establishing a plurality of mating subtypes for a line;
determining a percentage of progeny that are male for each of the mating subtypes, or a percentage of progeny that are female for each of the mating subtypes, that would result, relative to a control, in an increase in genetic merit in the line;
sorting a sperm cell sample from a male swine in one of the mating subtypes into one or more subpopulations of sperm cells, wherein at least 60% of sperm cells in a subpopulation of sperm cells bear X chromosomes or Y chromosomes; and
fertilizing one or more eggs from one or more female swine in the one of the mating subtypes with the subpopulation of sperm cells to achieve the percentage of progeny that are male, or the percentage of progeny that are female, determined to increase genetic merit relative to the control.

F1. The method of F, wherein the step of fertilizing is done in vivo.

F2. The method of F, wherein the step of fertilizing is done in vitro.

F3. The method of any of F to F2, wherein the percentage of progeny that are male, or the percentage of progeny that are female, determined to increase genetic merit, does not increase inbreeding in the line relative to the control.

F4. The method of any of F to F3, wherein the line comprises a sire line or dam line.

F5. The method of any of F to F4, wherein in the control, approximately 50% of progeny are male.

F6. The method of any of F to F5, wherein in the control, all female swine to be mated are inseminated with unsorted semen samples.

F7. The method of any of F to F6, wherein a category of male swine in one or more of the mating subtypes is defined by one or more characteristics, including genetic merit or age.

F8. The method of any of F to F7, wherein a category of female swine in one or more of the mating subtypes is defined by one or more characteristics, including genetic merit or parity.

F9. The method of any of F to F8, wherein the percentage of sperm cells in the subpopulation of sperm cells that bear X chromosomes or Y chromosomes is selected from the group consisting of at least 65%, at least 70%, at least 75%, at least 80%, at least 85%, at least 90%, at least 95%, at least 96%, at least 97%, at least 98%, at least 99% and at least 100%.

F10. The method of any of F to F9, wherein the line comprises a sire line and the percentage of progeny that are male for each of the mating subtypes, or the percentage of progeny that are female for each of the mating subtypes, determined to increase genetic merit of the line relative to a control, results in a percentage of progeny that are male for the line that is between approximately 10 to 35%.

F11. The method of F10, wherein the percentage of progeny that are male for the line is between approximately 15 to 30%.

F12. The method of any of F to F9, wherein the line comprises a dam line and the percentage of progeny that are male for each of the mating subtypes, or the percentage of progeny that are female for each of the mating subtypes, determined to increase genetic merit of the line relative to a control, results in a percentage of progeny that are male for the line that is between approximately 5 to 30%.

F13. The method of F12, wherein the percentage of progeny that are male for the line is between approximately 10 to 25%.

F14. The method of any of F to F9, wherein the percentage of progeny that are male for each of the mating subtypes, or the percentage of progeny that are female for each of the mating subtypes is between approximately 0 to 10% or between approximately 90 to 100% and the produced progeny are members of a daughter nucleus or a multiplier.

F15. The method of any of F to F14, wherein each of the mating subtypes in the plurality of mating subtypes comprises only one male swine or only one female swine from the line.

F16. The method of any of F to F15, wherein each of the mating subtypes in the plurality of mating subtypes comprises only one male swine and only one female swine from the line.

F17. The method of any of F to F16, wherein the determined percentages are determined using a stochastic or a deterministic method.

F18. The method of any of F to F17, wherein genetic merit of a male or a female is a function of one or more dam line traits.

F19. The method of any of F to F17, wherein genetic merit of a male or a female is a function of one or more sire line traits.

F20. The method of any of F to F17, wherein genetic merit of a male or a female is a function of a selection index.

F21. The method of any of F to F17, wherein genetic merit of a male or a female is a function of EBV.

F22. The method of F20, wherein the selection index is a function of data derived from a group comprising the male or the female.

F23. The method of F18, wherein the traits comprise fertility, litter size and milk production.

F24. The method of F19, wherein the traits comprise feed efficiency, average daily gain and carcass lean.

F25. The method of any of F to F24, comprising the additional step of selecting parents based on phenotypic measurement.

F26. The method of any of F to F24, comprising the additional step of selecting parents for the line based on genotype.

F27. The method of any of F to F24, comprising the additional step of selecting parents using mutation assisted selection.

F28. The method of any of F to F27, wherein the male swine or the one or more female swine are members of a genetic nucleus, a daughter nucleus or a multiplier.

F29. The method of any of F to F27, wherein the male swine or the one or more female swine are members of a genetic nucleus.

F30. The method of any of F to F29, wherein the step of establishing a plurality of mating subtypes for a line is performed as part of a breeding program.

F31. The method of any of F to F29, wherein the step of establishing a plurality of mating subtypes for a line is performed as part of creating a mating plan for the line.

G. A method of increasing the genetic progress of a line or breed of swine comprising the steps of:
collecting a semen sample from a boar from said line or breed;
sorting said semen sample into at least two subpopulations of sperm cells, wherein at least 80% of a first subpopulation bears X-chromosomes or Y-chromosomes;
inseminating a sow from said line or breed with sperm cells from said first subpopulation;
producing offspring from said sow; and
calculating a selection index for one or more of said offspring;
selecting one or more of said offspring having a higher selection index compared to the average selection index for said line or breed to breed with a swine from said line or breed so as to increase the genetic progress of said line or breed.

G1. The method of G wherein said line or breed is a gilt line and said first subpopulation bears X-chromosomes.

G2. The method of G wherein said line or breed is a boar line and said first subpopulation bears Y-chromosomes.

G3. The method of G, wherein the selection index for one or more of said offspring is calculated based on data derived from a group comprising said offspring.

G4. The method of G, wherein said selection index for one or more of said offspring comprises measuring the traits of fertility, litter size and milk production.

G5. The method of G, wherein said selection index for one or more of said offspring comprises measuring the traits of feed efficiency, average daily gain and carcass lean.

G6. The method of G, wherein the step of inseminating a sow from said line or breed with sperm cells from said first subpopulation comprises administering said sperm cells to said sow's reproductive tract using a deep intrauterine catheter or a needle inserted through a membrane of said sow.

G7. The method of G6, wherein administering said sperm cells to said sow's reproductive tract using a deep intrauterine catheter comprises placing said sperm cells in one or more uterine horns.

G8. The method of G7, wherein said deep intrauterine catheter comprises a video camera or scope.

G9. The method of G7, further comprising the step of visualizing the deep intrauterine catheter via radiography or fluoroscopy while inserted in said sow's reproductive tract.

G10. The method of G7, wherein the total number of sperm cells administered is $1 \times 10^9$ or less sperm cells.

G11. The method of G6, wherein administering said sperm cells to said sow's reproductive tract using a needle inserted through a membrane of said sow comprises injecting said sperm cells into one or more oviducts of said sow's uterus.

G12. The method of G11, further comprising the step of visualizing said needle being inserted into said one or more oviducts via a laparoscope or video camera.

G13. The method of G11, wherein the total number of sperm cells administered is $1 \times 10^6$ or less sperm cells.

G14. The method of any one of G to G13, further comprising the step of synchronizing estrus or inducing timed ovulation in said sow by administering one or more hormone or hormone analogs to said sow.

G15. The method of G14, wherein said one or more hormone or hormone analogs comprises PG600, OvuGel, eCG, progestin, or hCG.

G16. The method of G14, wherein said one or more hormone or hormone analog is administered by a programmable device placed in the reproductive tract of said sow.

G17. The method of G14, further comprising the step of detecting ovulation in said sow by examining said females follicles.

G18. The method of G17, wherein said follicles are examined using ultrasound.

G19. The method of any one of G to G13 wherein said sow is a member of a genetic nucleus or multiplier herd.

G20. The method of any one of G to G13 wherein said boar is a member of a genetic nucleus or multiplier herd.

H. A method of increasing the genetic progress of a line or breed of swine comprising the steps of:
collecting a semen sample from a boar from said line or breed;

sorting said semen sample into at least two subpopulations of sperm cells, wherein at least 80% of a first subpopulation bears X chromosomes or Y chromosomes;
inseminating a sow from said line or breed with sperm cells from said first subpopulation;
producing offspring from said sow;
obtaining a value for a trait in one or more of said offspring; and
selecting one or more of said offspring having a value for said trait that is greater than or less than the average value for said trait in said line or breed to breed with a swine from said line or breed so as to increase the genetic progress of said line or breed.

H1. The method of H wherein said line or breed is a gilt line and said first subpopulation bears X-chromosomes.

H2. The method of H wherein said line or breed is a boar line and said first subpopulation bears Y-chromosomes.

I. A method of increasing the number of offspring of genetically superior boars in a swine herd or on a swine farm comprising:
establishing a subpopulation of one or more genetically superior boars from a population of boars in a herd or on a farm;
obtaining sperm cell samples from the one or more genetically superior boars;
preparing a plurality of sperm cell doses from each of the sperm cell samples;
administering one or more hormone or hormone analogs to a plurality of sows in said herd or on said farm in order to induce timed ovulation for each sow; and
inseminating the sows with one or more sperm cell doses using a deep intrauterine catheter or a laparoscopic procedure, wherein the one or more sperm cell doses administered to each sow together comprise a total of less than $1 \times 10^9$ sperm cells;
thereby increasing the number of offspring of genetically superior boars in a herd or on a farm.

J. A method of reducing the number of boars necessary for breeding in a swine herd or on a swine farm comprising:
establishing a subpopulation of one or more genetically superior boars from a population of boars in a herd or on a farm;
obtaining sperm cell samples from the one or more genetically superior boars;
preparing a plurality of sperm cell doses from each of the sperm cell samples;
administering one or more hormone or hormone analogs to a plurality of sows in said herd or on said farm in order to induce timed ovulation for each sow; and
inseminating the sows with one or more sperm cell doses using a deep intrauterine catheter or a laparoscopic procedure, wherein the one or more sperm cell doses administered to each sow together comprise a total of less than $1 \times 10^9$ sperm cells;
thereby reducing the number of boars necessary for breeding in the herd or on the farm.

J1. The method of claim I or J wherein genetically superior boars comprise boars with a higher selection index relative to other boars within the herd or on the farm.

K. A method for increasing the profitability of a swine herd or farm comprising:
determining whether a male pig or a female pig results in a higher net income per pig based on market conditions to which the herd or farm is subject;
collecting a semen sample from a boar;
sorting said semen sample into at least two subpopulations of sperm cells, wherein at least 80% of a first subpopulation bears X-chromosomes if the female pig results in a higher net income per pig or Y-chromosomes if the male pig results in a higher net income per pig;
inseminating a sow with sperm cells from said first subpopulation; and
producing offspring from said sow.

K1. The method of K, wherein the male pig is a barrow.

K2. The method of K, wherein the female pig is a gilt.

K3. The method of K, wherein the step of determining whether a male pig or a female pig results in a higher net income per pig under market conditions to which the herd or farm is subject comprises comparing a trait between male and female pigs wherein the trait is selected from any one of the following: feed conversion, body weight, average daily gain, carcass lean, loin depth, back fat depth, belly fat depth, fat free lean index, lean gain per day, feed cost per pig and jowl fat iodine value.

As can be easily understood from the foregoing, the basic concepts of the present invention may be embodied in a variety of ways. The invention involves numerous and varied embodiments using sex sorted sperm cells to increase the genetic progress of a line, including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

What is claimed is:

1. A method of increasing genetic progress of swine within a genetic nucleus comprising the steps of:
providing a population of swine in a sire line in the genetic nucleus;
establishing a subpopulation of males and females from the population of swine available for breeding and parenting progeny;
inseminating one or more females in the subpopulation with a sex sorted sperm cell sample from one or more males in the subpopulation so that approximately 10 to 35% of the progeny of the subpopulation are male, thereby increasing the genetic progress within the genetic nucleus.

2. The method of claim 1, wherein approximately 15 to 30% of the progeny are male.

3. A method of increasing genetic progress of swine within a genetic nucleus comprising the steps of:
providing a population of swine in a dam line in the genetic nucleus;
establishing a subpopulation of males and females from the population of swine available for breeding and parenting progeny;
inseminating one or more females in the subpopulation with a sex sorted sperm cell sample from one or more males in the subpopulation so that approximately 5 to 30% of the progeny of the subpopulation are male, thereby increasing the genetic progress within the genetic nucleus.

4. The method of claim 3, wherein approximately 10 to 25% of the progeny are male.

* * * * *